(12) United States Patent
Bezel et al.

(10) Patent No.: US 10,495,287 B1
(45) Date of Patent: Dec. 3, 2019

(54) NANOCRYSTAL-BASED LIGHT SOURCE FOR SAMPLE CHARACTERIZATION

(71) Applicant: KLA-Tencor Corporation, Milpitas, CA (US)

(72) Inventors: Ilya Bezel, Mountain View, CA (US); Lauren Wilson, San Jose, CA (US); Joshua Wittenberg, Fremont, CA (US); Matthew Derstine, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/861,460

(22) Filed: Jan. 3, 2018

Related U.S. Application Data

(60) Provisional application No. 62/441,881, filed on Jan. 3, 2017.

(51) Int. Cl.
*F21V 9/32* (2018.01)
*F21V 9/38* (2018.01)
*G01N 21/88* (2006.01)
*G01N 21/95* (2006.01)

(52) U.S. Cl.
CPC .......... *F21V 9/32* (2018.02); *F21V 9/38* (2018.02); *G01N 21/8806* (2013.01); *G01N 21/9501* (2013.01); *G01N 2201/061* (2013.01)

(58) Field of Classification Search
CPC ........ F21V 9/32; F21V 9/38; G01N 21/9501; G01N 2201/061
USPC ................ 356/237.1–237.6, 239.1–239.8
See application file for complete search history.

(56) References Cited

U.S. PATENT DOCUMENTS

| | | | |
|---|---|---|---|
| 4,999,014 A | 3/1991 | Gold et al. | |
| 5,181,080 A | 1/1993 | Fanton | |
| 5,608,526 A | 3/1997 | Piwonka-Corle et al. | |
| 5,877,859 A | 3/1999 | Aspnes et al. | |
| 5,999,310 A | 12/1999 | Shafer et al. | |
| 6,297,880 B1 | 10/2001 | Rosencwaig et al. | |
| 6,429,943 B1 | 8/2002 | Opsal et al. | |
| 7,525,649 B1 | 4/2009 | Leong et al. | |
| 8,377,333 B2 | 2/2013 | Ramprasad et al. | |
| 8,724,054 B2 | 5/2014 | Jones | |

(Continued)

FOREIGN PATENT DOCUMENTS

EP   1116036 B1   8/2004

OTHER PUBLICATIONS

Parker, Akweli, "How Laser-powered Headlights Work", HowStuffWorks.com, https://auto.howstuffworks.com/laser-powered-headlight.htm, published Nov. 7, 2011.

(Continued)

*Primary Examiner* — Tri T Ton
(74) *Attorney, Agent, or Firm* — Suiter Swantz pc llo

(57) ABSTRACT

A broadband illumination source is disclosed. The broadband illumination source may include a pump source configured to generate pump illumination. The broadband illumination also includes an active medium containing nanocrystals. The broadband illumination source includes pump illumination optics configured to direct pump illumination into the active medium. The active medium is configured to emit broadband illumination by down-converting a portion of the pump illumination via photoluminescence.

42 Claims, 16 Drawing Sheets

(56) References Cited

U.S. PATENT DOCUMENTS

| | | | |
|---|---|---|---|
| 9,279,774 | B2 | 3/2016 | Romanovsky et al. |
| 9,405,290 | B1 | 8/2016 | Malkova et al. |
| 2003/0010987 | A1 | 1/2003 | Banin et al. |
| 2007/0002465 | A1 | 1/2007 | Chuang et al. |
| 2009/0180176 | A1 | 7/2009 | Armstrong et al. |
| 2011/0186872 | A1* | 8/2011 | Kim .............. H01L 33/486 257/88 |
| 2013/0114085 | A1 | 5/2013 | Wang et al. |
| 2013/0181595 | A1 | 7/2013 | Bezel et al. |
| 2015/0049341 | A1* | 2/2015 | Fujii .............. H01S 5/06216 356/479 |
| 2015/0338212 | A1* | 11/2015 | Moreau .......... G01N 21/1717 356/600 |

OTHER PUBLICATIONS

Los Alamos Nat'l Lab., "Novel Materials", Nanotechnology and Advanced Spectroscopy Team, http://quantumdot.lanl.gov/novel.shtml, published 2011.

Butty, J., et al., "Room temperature optical gain in sol-gel derived CdS quantum dots", Applied Physics Letters, pp. 3224-3226, vol. 69, Issue 21, http://aip.scitation.org/doi/abs/10.1063/1.118017, published Nov. 18, 1996.

Kim, D. Y., et al, "PbSe Nanocrystal-Based Infrared-to-Visible Up-Conversion Device", Nano Letters, pp. 2109-2113, vol. 11, Issue 5, published 2011.

Klimov, V., et al.,"Single-exciton optical gain in semiconductor nanocrystals", Nature, vol. 447, pp. 441-446, Published May 24, 2007.

Riehle, F.S., et al., "Blue Luminescence and Superstructures from Magic Size Clusters of CdSe" Nano Letters, vol. 9, pp. 514-518, Published Jan. 13, 2009.

Bruchez, M. Jr., et al., "Semiconductor nanocrystals as fluorescent biological labels", Science, vol. 281, Issue 5385, pp. 2013-2016, Published Sep. 25, 1998.

Reiss, P. et al., "Core/Shell semiconductor nanocrystals", Small, vol. 5, Issue 2, pp. 154-168, Published Jan. 20, 2009.

Loukanov, A. et al., "Photoluminescence depending on the ZnS shell thickness of CdS/ZnS core-shell semiconductor nanoparticles", Colloids and Surfaces A: Physicochem. Eng. Aspects, vol. 245, pp. 9-14, Published 2004.

Peng, X. et al., "Epitaxial Growth of Highly Luminescent CdSe/CdS Core/Shell Nanocrystals with Photostability and Electronic Accessibility", J. Am. Chem. Soc., vol. 119, Issue 30, pp. 7019-7029, Published Jul. 30, 1997.

Makhal, A. et al., "Light Harvesting Semiconductor Core-Shell Nanocrystals: Ultrafast Charge Transport Dynamics of CdSe—ZnS Quantum Dots", J. Phys. Chem. C, vol. 114, Issue 1, pp. 627-632, Published Dec. 14, 2009.

Smith, A. et al., "Semiconductor Nanocrystals: Structure, Properties, and Band Gap Engineering", Accounts of Chemical Research, vol. 43, Issue 2, pp. 190-200, Published Apr. 2, 2009.

Murphy, C. et al., "Quantum Dots: A Primer", Applied Spectroscopy, vol. 56, Issue 1, pp. 16A-27A, Published Jan. 1, 2002.

Fanton, et al., "Multiparameter Measurements of Thin Films Using Beam-Profile Reflectometry," Journal of Applied Physics, vol. 73, Issue 11, p. 7035, Published Feb. 16, 1993.

Leng, J. et al., Simultaneous measurement of six layers in a silicon on insulator film stack using spectrophotometry and beam profile reflectometry, Journal of Applied Physics, vol. 81, Issue 8, pp. 3570-358, Published Apr. 15, 1997.

* cited by examiner

NANOCRYSTAL-BASED LIGHT SOURCE FOR SAMPLE CHARACTERIZATION

CROSS-REFERENCE TO RELATED APPLICATION

The present application claims the benefit under 35 U.S.C. § 119(e) of U.S. Provisional Application Ser. No. 62/441,881, filed Jan. 3, 2017, entitled NANOCRYSTAL LIGHT SOURCES FOR WAFER INSPECTION, naming Ilya Bezel, Lauren Wilson, Joshua Wittenberg, and Matthew Derstine as inventors, which is incorporated herein by reference in the entirety.

TECHNICAL FIELD

The present invention generally relates to broadband inspection systems, and, in particular, to broadband inspection systems implementing a nanocrystal-based light source.

BACKGROUND

As the density of semiconductor devices increases, so too does the demand for improved illumination sources for semiconductor inspection and metrology techniques and systems. One such illumination source includes a broadband light source. There currently exists a large selection of illumination sources that can be used in the visible and near-infrared spectral regions. Broadband light sources, such as discharge driven or laser-sustained plasma sources, are beneficial for imaging applications in wafer inspection. There are also very bright narrow band sources available in the form of lasers, such as a diode laser. Laser-pumped phosphorous is known to produce stable broadband output in the visible spectral region. Black body emission limits radiance of conventional light sources that rely on heated gas (e.g., plasma) or solid state bodies (e.g., tungsten lamps). In order to achieve the required radiance, temperatures higher than 50,000 K are needed. Radiance of conventional broadband light sources, such as plasma-based sources, is limited by the black-body limit at achievable temperatures. Despite higher temperatures generally achieved in laser-sustained plasmas, their radiance is also not sufficient for many inspection applications. Laser-based sources are not limited by black-body limits and are generally bright, but they typically are narrow band and coherent, which creates certain imaging difficulties, like speckle noise and sensitivity to film thickness, which are often not desirable for wafer inspection. Therefore, there exists a need for an improved broadband illumination source usable in inspection and/or optical metrology systems.

SUMMARY

A broadband illumination source is disclosed, in accordance with one or more embodiments of the present disclosure. In one embodiment, the broadband illumination source includes a pump source configured to generate pump illumination. In another embodiment, the broadband illumination source includes an active medium containing a plurality of nanocrystals. In another embodiment, the broadband illumination source includes one or more pump illumination optics. In another embodiment, the one or more pump illumination optics are configured to direct pump illumination into the active medium. In another embodiment, the active medium is configured to emit broadband illumination by down converting a portion of the pump illumination via photoluminescence.

An optical characterization system for performing inspection and/or metrology of a sample is disclosed, in accordance with one or more embodiments of the present disclosure. In one embodiment, the system includes a broadband illumination source. In another embodiment, the broadband illumination sources includes a pump source configured to generate pump illumination; an active medium containing a plurality of nanocrystals; one or more pump illumination optics configured to direct pump illumination into the active medium, wherein the active medium is configured to emit broadband illumination by down converting a portion of the pump illumination via photoluminescence; and one or more source collection optics configured to collect a portion of the broadband illumination from the active medium. In another embodiment, the system includes a detector assembly. In another embodiment, the system includes a set of characterization optics configured to direct the broadband illumination from the broadband illumination source onto a sample, wherein the set of characterization optics is further configured to direct illumination from the sample to the detector assembly.

A method for generating and using broadband illumination in sample inspection and/or metrology is disclosed, in accordance with one or more embodiments of the present disclosure. In one embodiment, the method includes generating a pump beam. In another embodiment, the method includes directing the pump beam into an active medium containing a plurality of nanocrystals. In another embodiment, the method includes generating broadband illumination by down-converting a portion of the pump illumination with the plurality of nanocrystals via photoluminescence. In another embodiment, the method includes collecting down-converted broadband illumination from the active medium.

It is to be understood that both the foregoing general description and the following detailed description are exemplary and explanatory only, and are not necessarily restrictive of the invention as claimed. The accompanying drawings, which are incorporated in and constitute a part of the specification, illustrate embodiments of the invention and, together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

The present disclosure relates to improved methods and systems for semiconductor metrology and inspection systems. The following description is presented to enable one of ordinary skill in the art to make and use embodiments of the present disclosure as provided in the context of a particular application and its requirements. As used herein, directional terms such as "top," "bottom," "over," "under," "upper," "upward," "lower," "down," "downward," and the like, are intended to provide relative positions for purposes of description, and are not intended to designate an absolute frame of reference. Various modifications to the described embodiments will be apparent to those with skill in the art, and the general principles defined herein may be applied to other embodiments. Therefore, the present disclosure is not intended to be limited to the particular embodiments shown and described, but is to be accorded the widest scope consistent with the principles and novel features herein disclosed.

Referring generally to FIGS. 1 through 9, a system and method for the generation of broadband illumination is described, in accordance with one or more embodiments of the present disclosure. Embodiments of the present disclosure are directed toward generating and/or using broadband visible and/or IR radiation (e.g., near IR) in order to inspect, measure, or otherwise image various characteristics (e.g., defects) of a sample (e.g., semiconductor wafer).

Figure 1:
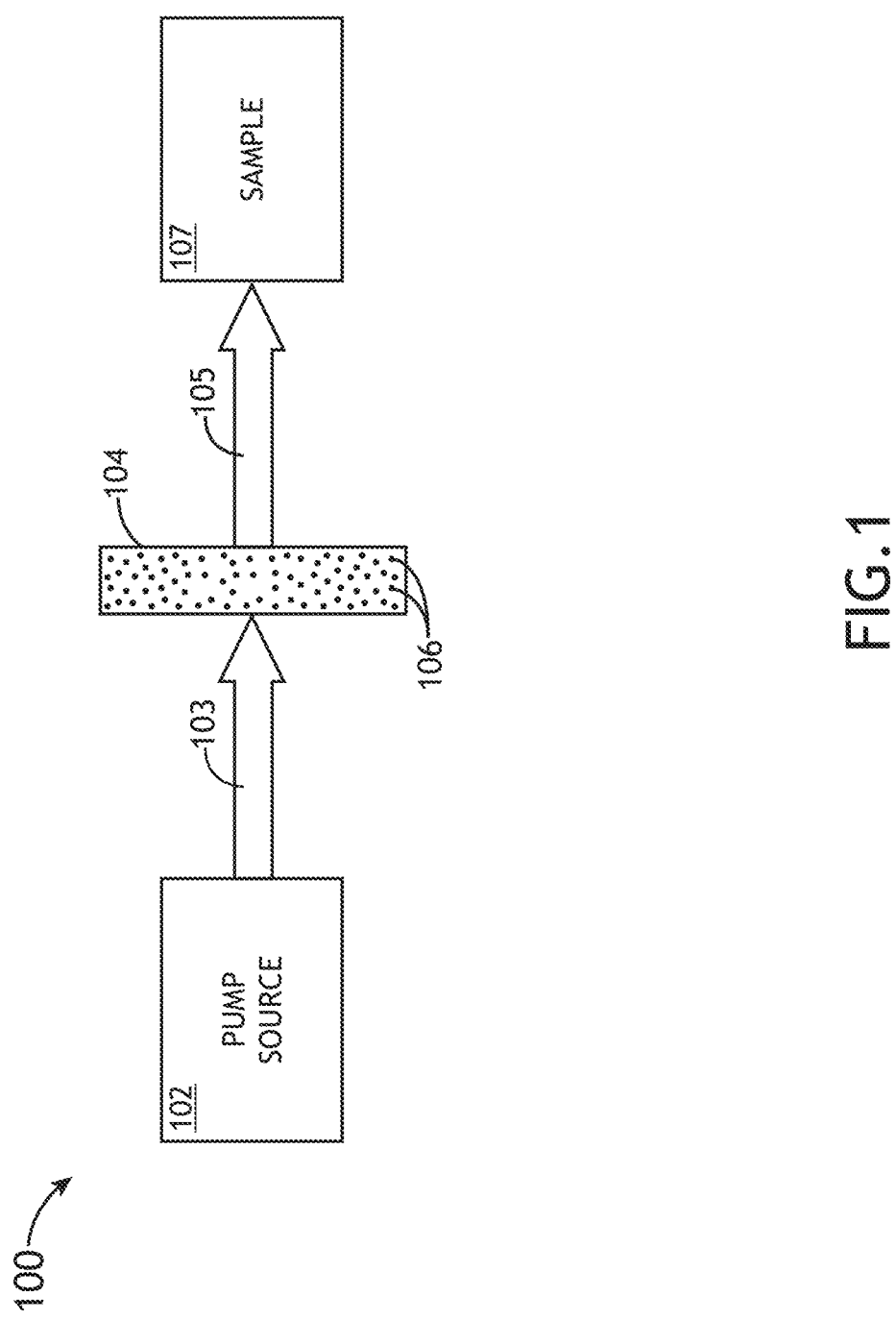
FIG. 1 illustrates a conceptual view of a broadband source for generating broadband illumination, in accordance with one more embodiments of the present disclosure.

FIG. 1 illustrates a conceptual view of a broadband source 100 for generating broadband illumination, in accordance with one more embodiments of the present disclosure.

In one embodiment, the broadband source 100 includes a pump source 102 configured to generate a pump beam 103. The pump beam 103 is directed to the active medium 104. In another embodiment, the active medium 104 contains a selected concentration or amount of one or more nanocrystal materials or semiconductor quantum dot materials. For the remainder of the present disclosure, the terms nanocrystals and quantum dots are used interchangeably. In one embodiment, the nanocrystals 106 of the active medium 104 absorb light from the pump beam 103 and down-convert light from the pump beam via one or more photoluminescence processes so as to generate output beam 105 that is red-shifted relative to the input pump beam 103. It is noted that nanocrystals/quantum dots generally display a short photoluminescence time (i.e., 1-100 ns), high quantum efficiency of photoluminescence, and good stability. By way of example, the nanocrystals 106 contained within a given active medium 104 may down-convert green and/or blue pump illumination 103 into visible and/or NIR broadband illumination 105. In turn, the down-converted illumination emitted by the active medium 104 may be collected and directed to a sample 107 for purposes of optically characterizing the sample 107. As discussed in more detail further herein, the broadband output from the active medium 104 may be tuned via the selection of the composition and sizes of nanocrystals 106.

Although much of the present disclosure is focused on pump illumination in the visible spectrum and a broadband emission in the visible and near-infrared spectrum, these spectral ranges should not be interpreted as a limitation on the scope of the present disclosure. It is noted herein that the scope of the present disclosure may extend to any type (e.g., composition and size) of nanocrystals/quantum dots capable of emitting illumination in any spectral range and a pump source having a spectral range capable of pumping such nanocrystals/quantum dots.

Figure 2:
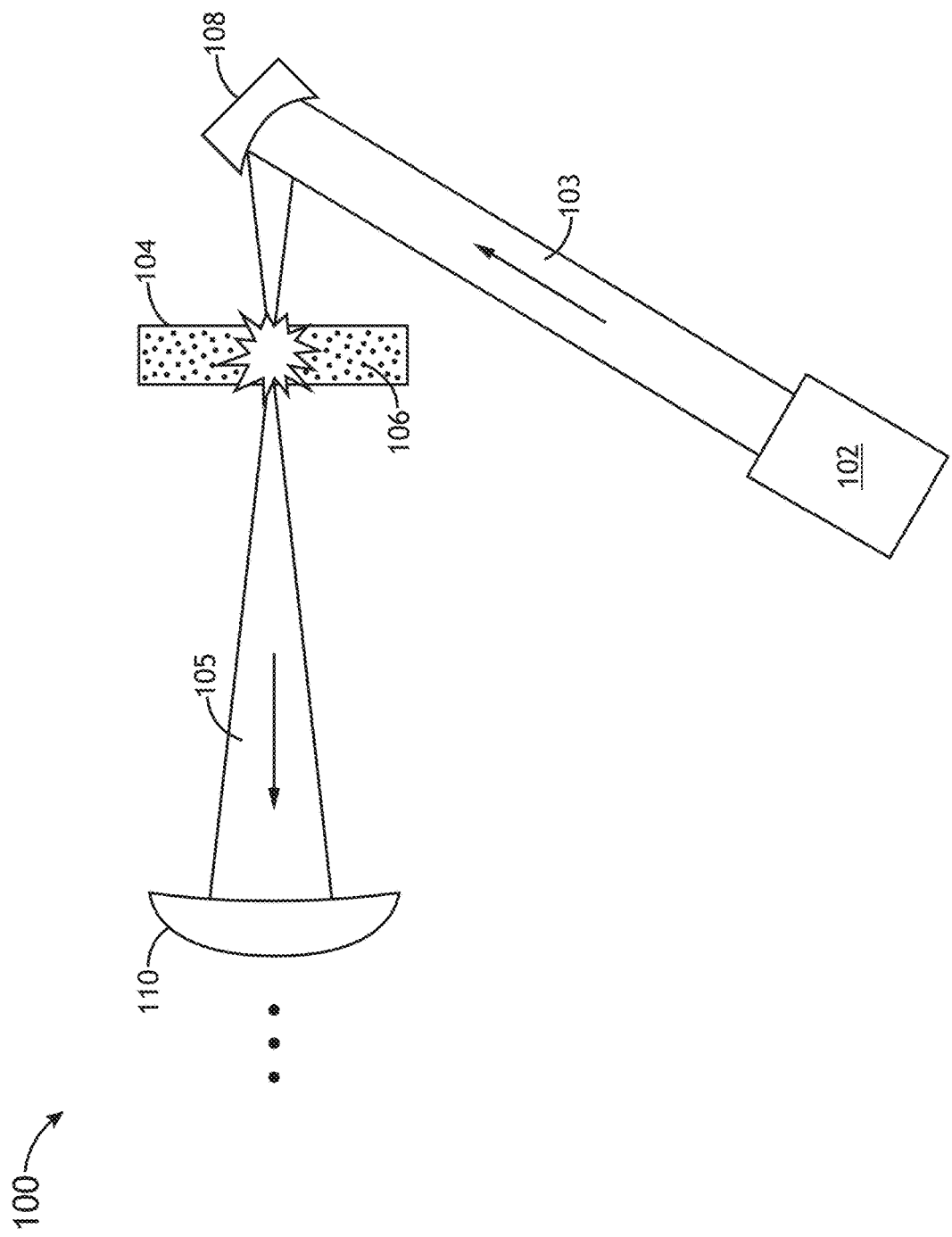
FIG. 2 illustrates a simplified schematic view of a broadband source for generating broadband illumination, in accordance with one more embodiments of the present disclosure.

FIG. 2 illustrates a simplified schematic view of the broadband source 100 for generating broadband illumination, in accordance with one more embodiments of the present disclosure. In one embodiment, the broadband source 100 includes one or more pump illumination optics 108 for directing and/or focusing pump illumination 103 from the pump source 102 into the active medium 104. The pump illumination optics 108 may include any optical element known in the art including, but not limited to, one or more lenses, one or more mirrors, one or more filters, one or more gratings, and the like. As depicted in FIG. 2, a focusing mirror may focus the pump illumination 102 into the volume of the active medium 104, allowing the nanocrystals 106 to absorb the pump illumination 103. The nanocrystals 106 may then down-convert light from the pump beam 103 via one or more photoluminescence processes so as to generate the broadband output 105. In another embodiment, the broadband source 100 includes one or more collection optics 110. The collection illumination optics 110 may include any optical element known in the art including, but not limited to, one or more lenses, one or more mirrors, one or more filters, one or gratings, and the like. In one embodiment, the one or more collection optics 110 are configured to collect a portion of the broadband illumination emitted from the nanocrystals 106 and direct the broadband illumination to one or more additional optical elements. For example, as discussed further herein, the collection optics 110 of the broadband source 100 may be used to couple the output of the broadband source 100 to the illumination optics of an inspection tool or metrology tool for characterizing the sample 107.

The pump source 102 may include any illumination source known in the art. In one embodiment, the pump source 102 includes one or more laser sources. For example, the pump source 102 may include, but is not limited to, one or more laser sources configured to emit light between 350-750 nm. For example, pump source 102 may include, but is not limited to, a visible laser source. For instance, the pump source 102 may include, but is not limited to, a laser source configured to emit blue or green light. For instance, the pump source 102 may include a CW laser, such as, but not limited to, a YAG laser (e.g., 532 nm $2^{nd}$ harmonics of NdYAG laser) or a solid state laser (e.g., GaN laser).

In another embodiment, the nanocrystals contained with the active medium may be selected (e.g., based on composition and/or size) to emit light in the visible and/or infrared (e.g., NIR) wavelength range in response to the pump illumination 103. For example, the nanocrystal composition may be selected so as to emit visible-NIR light (e.g., 380-2500 nm). For instance, CdSe nanocrystals stimulated by violet or blue visible light (e.g., 380-495 nm) may emit visible and/or NIR light in the 400 to 750 nm range.

It is noted that the scope of the present disclosure is not limited to the down-conversion of pump light or the wavelength range described above. The scope of the present disclosure may be extended to any composition and/or size of nanocrystals capable of emitting illumination in the visible-IR spectrum in response to a pump beam.

In one embodiment, the active medium 104 is a liquid. In this regard, the active medium 104 may include a mixture of the nanocrystals and a liquid material. For example, the nanocrystals and liquid may form a solution, a suspension, or a colloid. For example, the nanocrystals 106 may be suspended in a selected liquid to form the active medium 104. By way of another example, the nanocrystals 106 may be a colloidal mixture in a selected liquid to form the active medium 104.

In another embodiment, the active medium 104 is a solid material. For example, the nanocrystals 106 may be formed within a solid matrix within the active medium 104. The active medium 104 may be formed in any materials processing manner known in the art. In one embodiment, the active medium 104 containing the nanocrystals 106 may be formed via a sol-gel process technique. The fabrication of quantum dots/nanocrystals via sol-gel processing is described in J. Butty et al. "Room temperature optical gain in sol-gel derived CdS quantum dots" *Appl. Phys. Lett.* 69, 3224 (1996), which is incorporated herein by reference.

In another embodiment, the active medium 104 is a glass. For example, the nanocrystals 106 may be formed within a glass matrix within the active medium 104. In another embodiment, as discussed further herein, a solid or glass active media 104 may be formed on one or more substrates.

It is noted herein that the emission and absorption spectrum of the active medium 104 may be controlled or tuned by the selection of the materials used in the nanocrystals 106 and/or the size of the nanocrystals. In this regard, a particular active medium 104 may be tuned by including nanocrystals 106 from a selected material (or materials) and size (or sizes) to achieve the desired emission spectrum from the active medium 104.

The active medium 104 may incorporate any type of nanocrystal or quantum dot material known in the art. For example, the nanocrystals 106 used to form the active medium 104 may include, but are not limited to, CdSe, CdS, PbS, ZnSe, and/or CdTe. In another embodiment, the nanocrystals 106 may include core/shell nanocrystals, whereby one material forms the core of the nanocrystal and an additional material forms the shell of the nanocrystal. Core-Shell nanocrystals are particularly useful because they display high photoluminescence quantum yields, stability, large thermal range, and also can be put in various matrices without a large effect on their emission properties. The active medium 104 may incorporate any core-shell or core-shell-shell nanocrystal configuration known in the art. For example, core-shell nanocrystals may be formed from type II-VI; IV-VI; and III-V semiconductor materials (notation is core material-shell material). Such core-shell materials may include, but are not limited to, CdS—ZnS, CdSe—ZnS, CdSe—CdS, InAs—CdSe, PbSe—CdSe. A core-shell-shell configuration may include, but is not limited to, PbSe/CdSe/CdS (i.e., PbSe is core material, CdSe is inner shell material, CdS is outer shell material). It is noted that the listings of core-shell materials and core-shell-shell materials provided above should not be interpreted as limiting in any way on the scope of the present disclosure as it is recognized that any of a number of core material-shell material combinations may be used in the context of the present disclosure.

As noted previously herein, the particular emission and absorption spectrum from the active medium 104 and the nanocrystals 106 may be controlled by controlling the size, and thus the quantum confinement, of the nanocrystals. In one embodiment, the nanocrystals may have an average diameter between approximately 1 and 10 nm. For example, in the case of CdSe, nanocrystals having a diameter of approximately 2 nm may emit blue light, while nanocrystals having a diameter of approximately 8 nm may emit deep red light, with intermediate-sized nanocrystals emitting light between blue light and deep red light. It is noted that this effect is observed in numerous nanocrystal materials across various size ranges and the scope of the present disclosure is not in any way limited to CdSe or the size range 2-8 nm.

In another embodiment, the active medium 104 may contain a mixture of nanocrystal 106 species or may include discrete regions of different types of nanocrystal species.

In some embodiments, the active medium 104 may be formed by fabricating a set of monolayers on a substrate. By way of example, in the case of a set of monolayers, in order to achieve a radiance of 1 W/mm$^2$/srad/nm, nanocrystals of approximately 10 nm must emit 126 W uniformly in all direction from a 1 mm$^2$ sample. Such a configuration corresponds to approximately 8×10$^{20}$ photons/s in the 1000 nm wavelength range. If it is assumed that the photoluminescence lifetime is 20 ns and the photoluminescence quantum yield is approximately 50% then approximately 3×10$^{13}$ nanocrystals/mm$^2$ are needed to achieve the desired radiance. It is noted that nanocrystals can be tightly packed with surface/area densities of approximately $2\times10^{12}$ nanocrystals/$mm^2$. Therefore, a density on the order of $10^{13}$ may be achieved by stacking multiple monolayers (e.g., approximately 10 or more), which allows for the desired radiance. It is further noted that the pump power of approximately 0.5 $kW/mm^2$ is easily achievable with current lasers. It is noted that a liquid active medium may aid in the dissipation of such power. However, solid active media may be suitable, especially in configurations which provide for additional thermal management capabilities as discussed further herein.

Nanocrystals suitable for implementation in the broadband source 100 are described in Riehle, F. S.; Bienert, R.; Thomann, R.; Urban, G. A.; Kruger, M., "Blue luminescence and superstructures from magic size clusters of CdSe" *Nano Lett.* 2009, 9, 514-518; Bruchez, M., Jr.; Moronne, M.; Gin, P.; Weiss, S.; Alivisatos, A. P., "Semiconductor nanocrystals as fluorescent biological labels" Science 1998, 281, 2013-2016; Reiss, Peter; Protière, Myriam; Li, Liang, "Core/Shell Semiconductor Nanocrystals" *Small.* 5 (2): 154-168; Loukanov, Alexandre R.; Dushkin, Ceco D.; Papazova, Karolina I.; Kirov, Andrey V.; Abrashev, Miroslav V.; Adachi, Eiki "Photoluminescence depending on the ZnS shell thickness of CdS/ZnS core-shell semiconductor nanoparticles" *Colloids and Surfaces A: Physicochemical and Engineering Aspects.* 245 (1-3): 9-14; Peng, Xiaogang; Schlamp, Michael C.; Kadavanich, Andreas V.; Alivisatos, A. P. "Epitaxial Growth of Highly Luminescent CdSe/CdS Core/Shell Nanocrystals with Photostability and Electronic Accessibility" Journal of the American Chemical Society. 119 (30): 7019-7029; Makhal, Abhinandan; Yan, Hongdan; Lemmens, Peter; Pal, Samir Kumar "Light Harvesting Semiconductor Core-Shell Nanocrystals: Ultrafast charge transport dynamics of CdSe—ZnS quantum dots" *The Journal of Physical Chemistry C.* 114 (1): 627-632; Smith, Andrew M.; Nie, Shuming "Semiconductor nanocrystals: structure, properties, and band gap engineering" *Accounts of Chemical Research* 43 (2): 190-200; and Murphy, C. J. and Coffer, J. L. "Quantum dots: a primer" *Appl. Spectrosc.* 2002, 56, 16A-27A, which are each incorporated herein by reference in their entirety. Semiconductor nanocrystalline materials are described in U.S. Patent Publication No. 2003/0010987, published on Jan. 16, 2003; and U.S. Pat. No. 8,377,333, issued on Feb. 19, 2013, which are each incorporated herein by reference in their entirety.

Figure 3A:
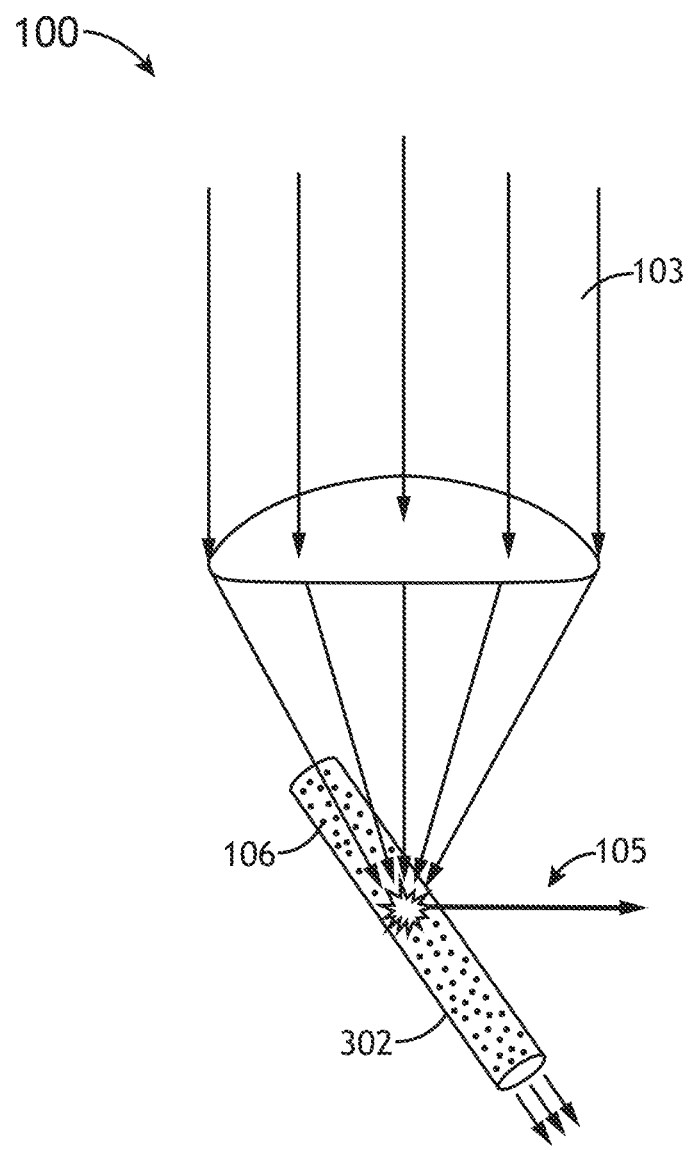
FIG. 3A illustrates a simplified schematic view of a broadband source utilizing a jet of liquid containing nanocrystals suspended as an active medium, in accordance with one more embodiments of the present disclosure.

FIG. 3A illustrates a simplified schematic view of the broadband source 100 incorporating a liquid jet 302 as the active medium 104, in accordance with one more embodiments of the present disclosure. In this embodiment, the liquid-based active medium (e.g., solution, suspension, or colloid) contains nanocrystals 106 and may be flowed along a selected direction in the liquid jet 302, thereby carrying the nanocrystals through the pump illumination 103. In turn, the pump illumination 103 may be down-converted by the nanocrystals 106 contained within the liquid jet 302 with the down-converted broadband radiation 105 being emitted along a given collection direction. It is noted that such an arrangement aids in the dissipation of power within the active medium 104, which provides for thermal management of the source 100.

In some embodiments, high radiance may be achieved in limited etendue settings through selected configurations of the active media and the pump illumination 103. In one embodiment, the active medium 104 may be transversely pumped with the pump illumination 103. For example, pump illumination 103 (e.g., laser beam) may be focused to a line on a surface and/or into a capillary structure containing the active medium. In another embodiment, the active medium 104 may be longitudinally pumped with the pump illumination 103. For example, pump illumination 103 (e.g., laser beam) may be focused into a cylindrical volume. In these cases, higher radiance may be attained along the longitudinal direction of the pumped volume. Such a configuration provides reduced pump fluence levels, allows for increased volume of the active medium, reduces the thermal load per unit volume of the active medium, and/or aids in the thermal management of the active medium.

Figure 3B:
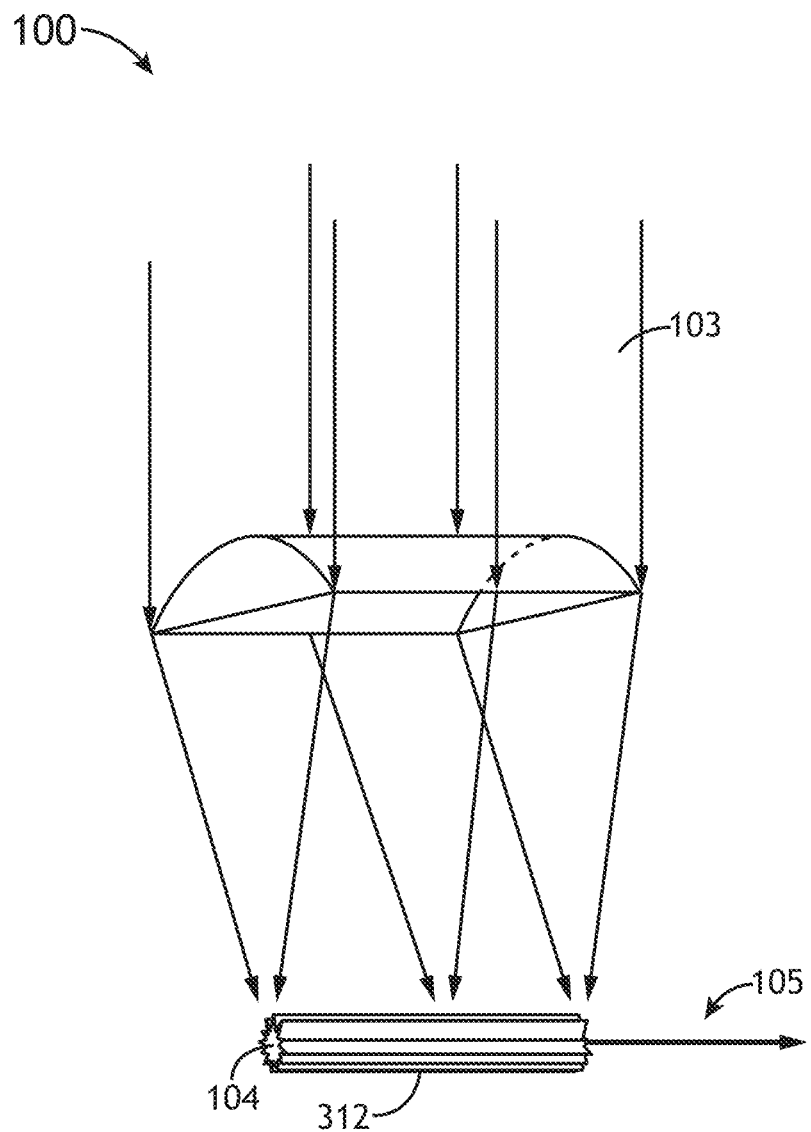
FIG. 3B illustrates a simplified schematic view of transversally pumped nanocrystals contained within a capillary structure of the active medium, in accordance with one more embodiments of the present disclosure.

FIG. 3B illustrates a simplified schematic view of transversely pumped nanocrystals contained within a capillary of the active medium, in accordance with one more embodiments of the present disclosure. As shown in FIG. 3B, pump illumination 103 may be transversely focused/directed into an elongated spot or spots (e.g., forming a line) into a capillary structure 312 or a film structure, which contains the nanocrystals. In this embodiment, the broadband illumination 105 emitted by the active medium 104 may have a higher radiance along the longitudinal direction of the pumped active medium.

Figure 3C:
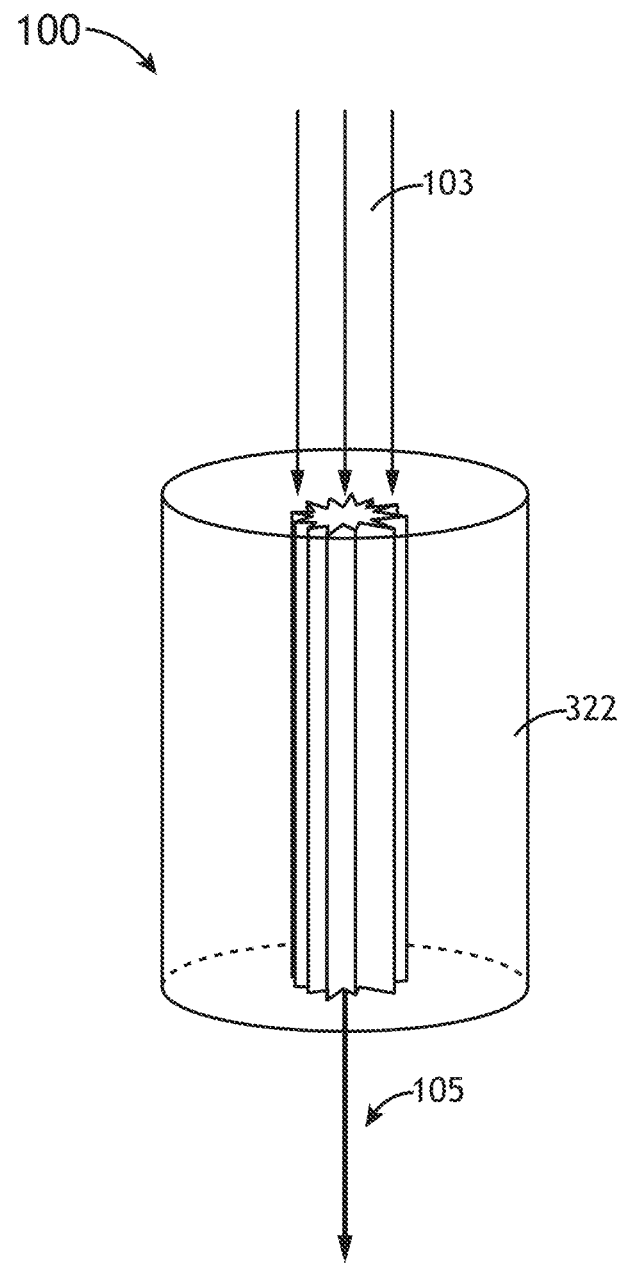
FIG. 3C illustrates a simplified schematic view of longitudinally pumped nanocrystals contained within a cylindrical volume of the active medium, in accordance with one more embodiments of the present disclosure.

FIG. 3C illustrates a simplified schematic view of longitudinally pumped nanocrystals contained within a cylindrical volume of the active medium, in accordance with one more embodiments of the present disclosure. As shown in FIG. 3C, pump illumination 103 may be longitudinally focused/directed into a cylindrical volume 322 (or other shape) of the active medium 104. For instance, the volume of active medium 104 may include a dye-cell containing the nanocrystal-containing active medium 104. The broadband illumination 105 emitted by the active medium 104 may have a higher radiance along the longitudinal direction of the pumped active medium.

Figure 4A:
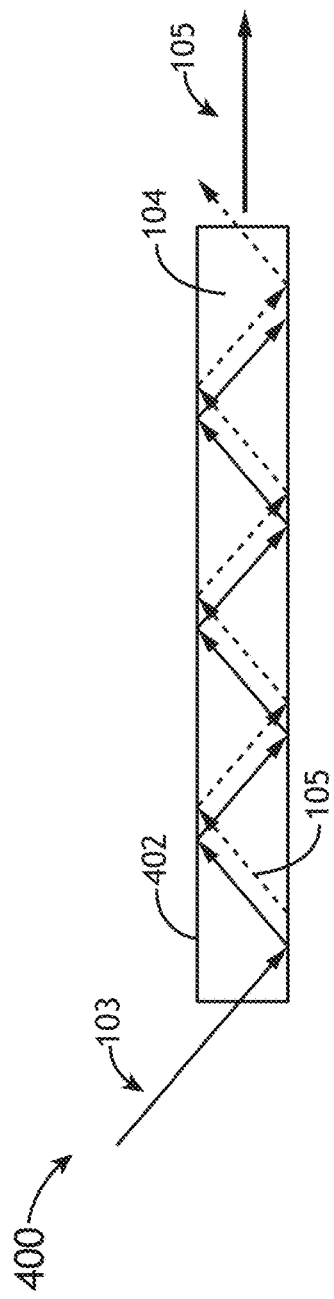
FIG. 4A illustrates a simplified schematic view of a waveguide arrangement, whereby the pump illumination and the broadband illumination is directed along the elongated active medium, in accordance with one more embodiments of the present disclosure.
Figure 4B:
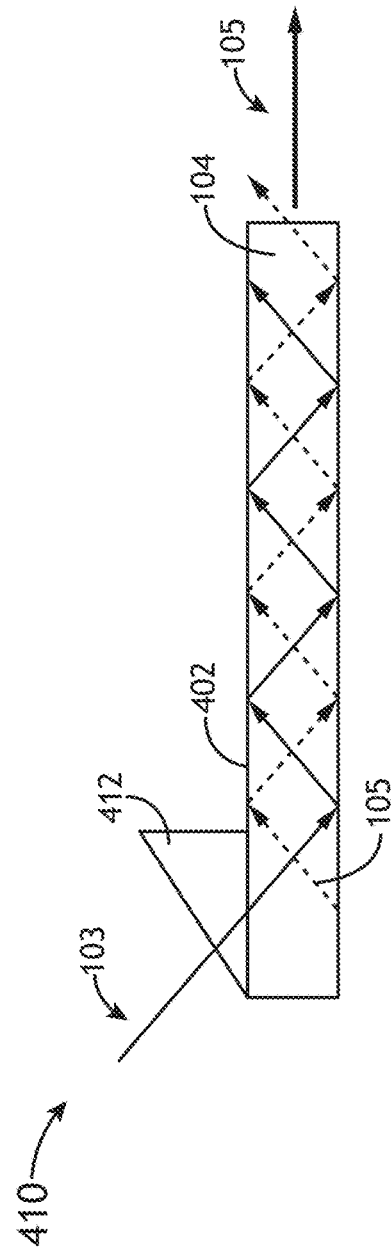
FIG. 4B illustrates a simplified schematic view of a waveguide arrangement including a coupling prism for introducing pump illumination into the active medium, in accordance with one more embodiments of the present disclosure.

FIGS. 4A-4B illustrate a waveguide arrangement 400, whereby the pump illumination and the broadband illumination are directed along the elongated active medium 104, in accordance with one more embodiments of the present disclosure. For example, an active media 104 may be implemented that displays a refractive index sufficient to establish a wave-guide mode within an elongated volume 402 for the selected pump illumination 103. For instance, as shown in FIG. 4A, the pump source 102 and the elongated volume 402 of active medium 104 may be arranged such that the pump illumination 103 is coupled into the elongated volume 402. The elongated volume 402 may include a cylindrical volume of active medium 104, a capillary structure containing the active medium 104, or a film of active medium 104. In this regard, pump illumination 103 of a selected spectral content may be used to pump the active media 104 by exciting one or more wave-guide modes within the active medium 104 having a high-refractive index (e.g., higher than surrounding air or atmosphere). In this embodiment, pump illumination 103 and down-converted broadband illumination 105 emitted by the nanocrystals 106 of the active medium 104 both propagate along the elongated volume 402.

In another embodiment, as illustrated in FIG. 4B, the source 100 includes a coupling element 412 arranged to couple the pump illumination 103 into the elongated volume 402 of active medium 104. It is noted that the pump illumination 103 from the pump source 102 may be coupled into the elongated volume 402 in any manner known in the art. For example, the coupling element 412 may include, but is not limited to, a coupling prism, coupling lens, a coupling grating, and the like. By way of another example, the coupling element 412 may be arranged to couple the pump illumination 103 into the elongated volume 402 at the end of the elongated volume 402 and/or at a side of the elongated volume 402.

Figure 5A:
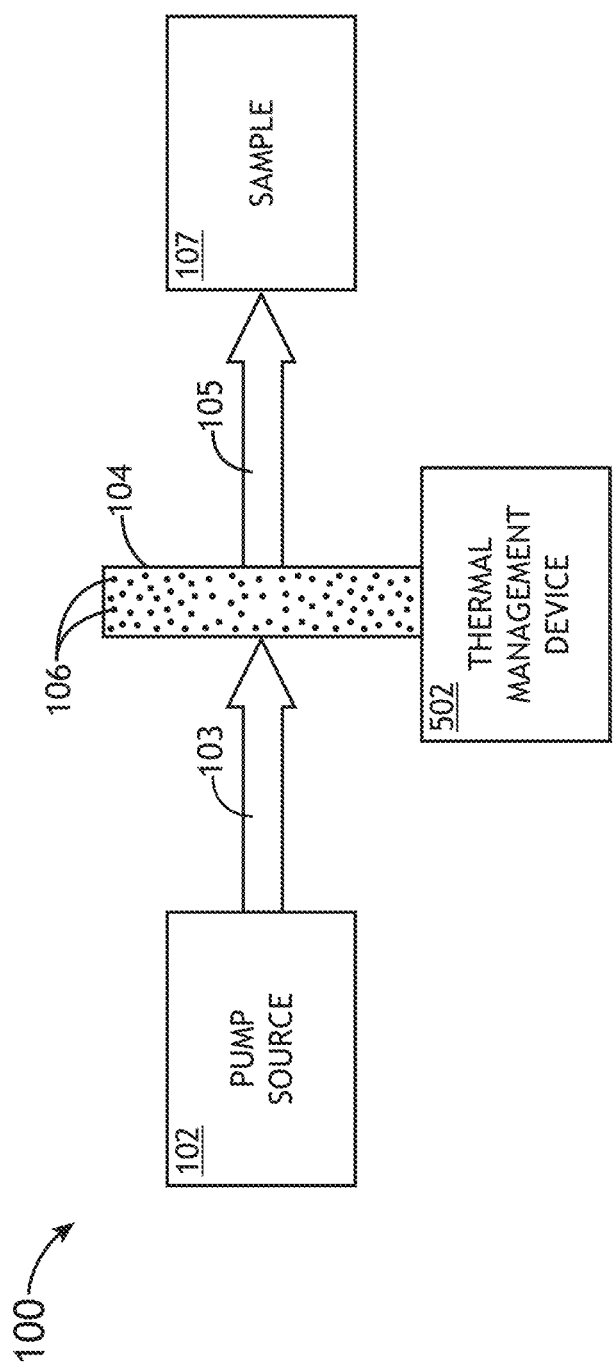
FIG. 5A illustrates a conceptual view of the broadband source equipped with a thermal management device, in accordance with one or more embodiments of the present disclosure.

FIG. 5A illustrates a conceptual view of the broadband source 100 equipped with a thermal management device 502, in accordance with one or more embodiments of the present disclosure. It is noted that the broadband source 100 may incorporate any device, sub-system, or mechanism suitable for providing thermal management of the active medium 104. Although various nanocrystals have shown to be resilient at temperatures above 200° C., in some settings thermal management capabilities may be desirable. In some embodiments, the thermal management device 502 may include a mechanical and/or electromechanical device for rotating, translating, or otherwise actuating the active medium 104 such that active medium 104 is moved relative to the pump illumination 103 to mitigate heating caused by the pump illumination 103. For example, the thermal management device 502 may include, but is not limited to, a movable substrate, whereby the active medium 104 is formed on the surface of or within a layer of the movable substrate.

Figure 5B:
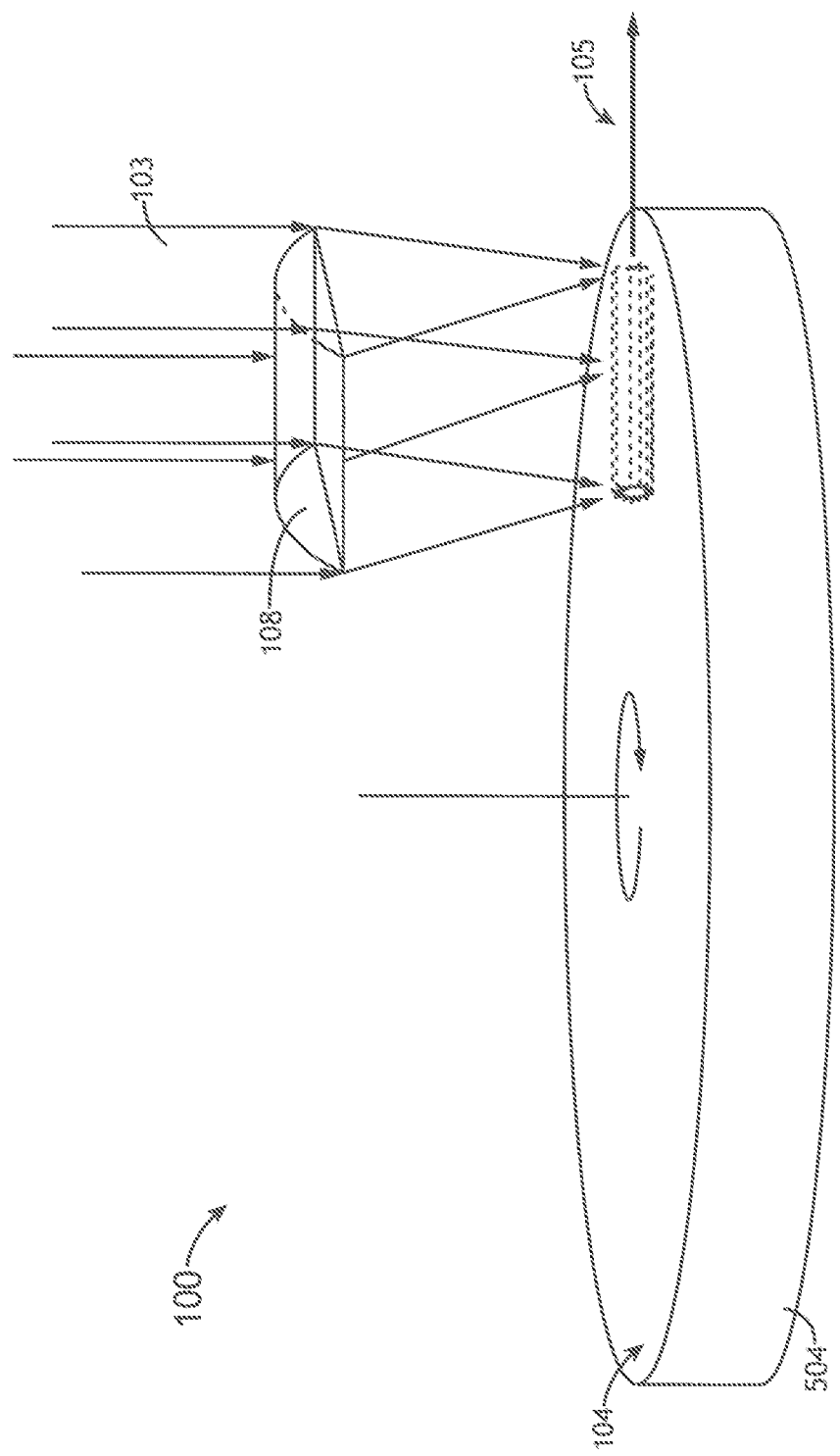
FIG. 5B illustrates a simplified schematic view of an active medium containing nanocrystals disposed on a rotatable substrate for thermal management of the active medium, in accordance with one more embodiments of the present disclosure.

FIG. 5B illustrates a simplified schematic view of the broadband source 100 incorporating a rotatable substrate 504 for thermal management of the active medium 104, in accordance with one more embodiments of the present disclosure. For example, the active medium 104 containing one or more nanocrystal materials 106 may be deposited on a surface of a rotatable substrate 504, such as, but not limited to, a rotatable disk. For instance, the nanocrystal materials 104 may be deposited on the rotatable substrate 504 via sol-gel processing. In the example depicted in FIG. 5B, pump illumination 103 may be delivered transversely to a portion of the active medium 104, providing for the preferential emission of down-converted broadband illumination 105 along the radial direction of the rotatable substrate 504. It is noted that the rotatable substrate 504 is not limited to a disk structure, which is provided merely for purposes of illustration. It is recognized herein that a mechanical thermal management device 502 may include any type of movable substrate and may come in any number of forms such as, but not limited to, a sphere, a cylinder or drum (see FIG. 6D), a ring, a conveyor, and the like.

In other embodiments, the thermal management device 502 may include a fluid transport device or sub-system used to flow a fluid active medium, such as a liquid active medium 104, relative to the pump illumination 103 to mitigate heating caused by the pump illumination 103. For example, a liquid jet of active medium 104, such as that depicted in FIG. 3A, may be used to establish and maintain a flow of active medium 104 relative to the pump illumination 103. It is further noted that any number of components may be used to establish such a liquid flow of active medium 104, such as, but not limited to, one or more liquid containers, channeling devices (e.g., tubes, hoses, etc.), pumps, and the like.

Figure 5C:
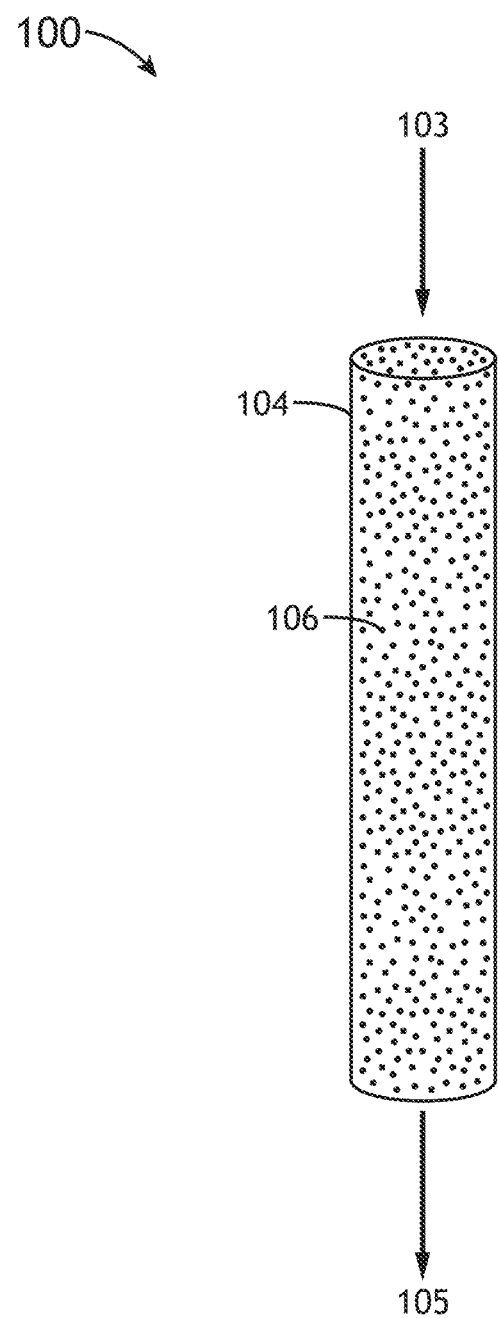
FIG. 5C illustrates a simplified schematic view of a fiber-based active medium containing nanocrystals embedded within the fiber-based active medium, in accordance with one more embodiments of the present disclosure.

FIG. 5C illustrates a simplified schematic view of a fiber-based active medium 104 containing nanocrystals embedded within the fiber-based active medium, in accordance with one more embodiments of the present disclosure. In one embodiment, the active medium 104 comprises one or more optical fibers impregnated with one or more nanocrystals 106. In another embodiment, the broadband source 100 may include multiple optical fibers, whereby each fiber (or each grouping of the fibers) is impregnated with a different nanocrystal species. In this example, pump illumination 103 from the pump source (not shown in FIG. 5C) may be delivered to the nanocrystal-impregnated fiber(s) via a coupling lens (not shown) (or other optical coupling element) used to couple pump illumination from the pump source into a fiber. In another embodiment, a non-impregnated optical fiber (not shown) (or a portion of a single fiber) may deliver the pump illumination 103 to the impregnated optical fiber (or a portion of the single fiber that is impregnated with the nanocrystals).

Figure 6A:
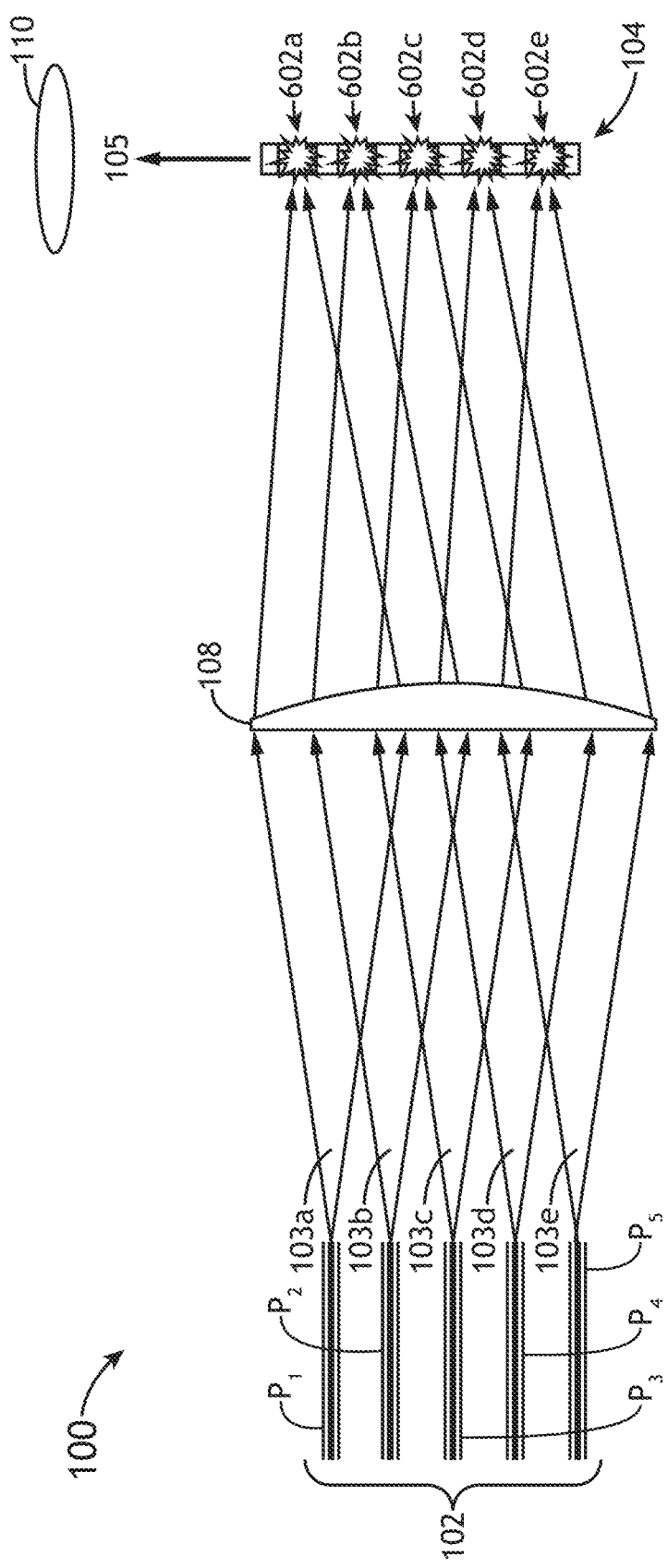
FIGS. 6A-6B illustrate a simplified schematic view of a broadband source including a set of lasers used to pump discrete emission regions of an active medium, in accordance with one more embodiments of the present disclosure.
Figure 6B:
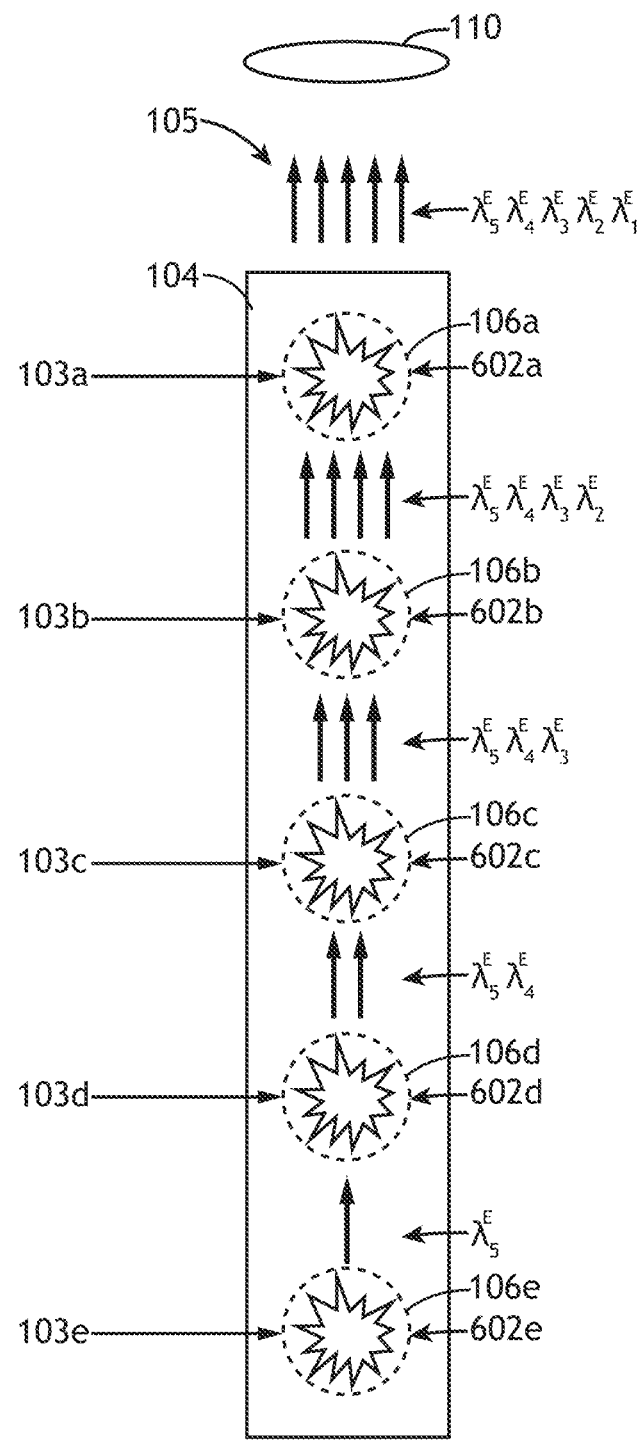

FIGS. 6A-6B illustrate a simplified schematic view of the broadband illumination source 100 including a set of lasers used to pump discrete emission regions of an active medium, in accordance with one more embodiments of the present disclosure. In one embodiment, as shown in FIG. 6A, the pump source 102 may include a plurality of laser sources P1, P2, P3, P4, P5 (and so on). For example, each laser may emit pump illumination at a different wavelength. For instance, in the case of laser sources P1-P5, the pump illumination beams may include pump beams having wavelengths $\lambda^P_1$, $\lambda^P_2$, $\lambda^P_3$, $\lambda^P_4$, and $\lambda^P_5$ respectively. In another embodiment, each of the pump beams 103a-103e may be focused and/or directed via one or more optical elements (e.g., lens, mirror, etc.) into a particular portion of the volume of the active medium 104 so as to create multiple emission regions/spots 602a, 602b, 602c, 602d, and 602e (and so on). Each emission region may be formed by nanocrystals of a selected nanocrystal species. For instance, each emission region may be formed by nanocrystals of a selected size and/or composition. In another embodiment, each of the emission regions 602a-602e may emit illumination of a different wavelength range. For example, the individual pump lasers P1-P5, the composition of the nanocrystals within each emission region of the active medium, and/or the size of the nanocrystals within each emission region of the active medium 104 may be selected so as to produce the desired output spectrum and/or absorption spectrum for each emission region 602a-602e. In this regard, the selection of the pump laser P1-P5s wavelengths, the composition of the nanocrystal-based emission regions, and/or the size of the nanocrystals within the emission regions may be controlled so as to tune the output of the emission regions 602a-602e.

In another embodiment, the direction of collection of broadband illumination from the emission regions 602a-602e may be generally perpendicular to the direction of the pump illumination 103a-103e from pump lasers P1-P5. For instance, in the case where the active medium 104 has an elongated structure (e.g., cylindrical) the pump illumination 103a-103e from the pump lasers P1-P5 may be directed to transversely pump the emission regions 602a-602e. In another embodiment, each emission region may then emit illumination that is down-converted relative to the respective pump illumination beams 103a-103e.

In another embodiment, the emission regions 602a-602e (and the volumes of nanocrystal species used to form them) may be arranged such that a first emission region (e.g., 602a), which emits a first wavelength or wavelength range, is located on a side of the collecting path nearest the collection optics 110, where at least an additional region (e.g., 602b-602e), which emits an Nth wavelength or wavelength range, is opposite to the first emission region, wherein the Nth wavelength or wavelength range is larger than the first wavelength or wavelength range.

In another embodiment, as shown in FIG. 6B, each of the nanocrystal species 106a-106e, which form the emission regions 602a-602e, may be selected such that each successive emissive region is at least partially transparent to the broadband illumination emitted by the previous emission region. In one embodiment, crystal size and/or material composition of the emission regions 602a-602e may be selected in such a way that redder-emitting emission regions are located on the far end of the light collection path and bluer-emitting emission regions are located on the near side of the light collecting path. In such an arrangement, the redder-wavelength light emitted by nanocrystals at the far end propagates through the active media of bluer-wavelength emitting nanocrystals and is not absorbed. In another embodiment, the light propagating in the opposite direction may be absorbed. It is noted that such an arrangement may be fabricated using the same nanocrystal material for each dot and controlling the size of the nanocrystals that make up each dot, with smaller nanocrystals used on the blue-side of the series of dots and larger nanocrystals used on the red-side of the series of dots. In the case of CdSe, it has been shown that a variation in nanocrystal size from 2 to 8 nm causes light emission to vary from violet/blue (on the 2 nm side) to deep red (on the 8 nm side).

For example, as shown in FIG. 6B, the nanocrystals 106e used to form emission region 602e down-convert the pump illumination 103e of wavelength $\lambda^P_5$ to emit broadband illumination having a central wavelength of $\lambda^E_5$, where $\lambda^E_5 > \lambda^P_5$. The nanocrystals 106d used to form emission region 602d down-convert the pump illumination 103d of wavelength $\lambda^P_4$ to emit broadband illumination having a central wavelength of $\lambda^E_4$, where $\lambda^E_4 > \lambda^P_4$. The nanocrystals 106d are selected such that the absorption spectrum of the nanocrystals 106d provides for at least the partial transmission of the broadband illumination containing $\lambda^E_5$.

The nanocrystals 106c used to form emission region 602c down-convert the pump illumination 103c of wavelength $\lambda^P_3$ to emit broadband illumination having a central wavelength of $\lambda^E_3$, where $\lambda^E_3 > \lambda^P_3$. In addition, the nanocrystals 106c are selected such that the absorption spectrum of the nanocrystals 106c provides for at least the partial transmission of the broadband illumination containing $\lambda^E_4$. The nanocrystals 106b used to form emission region 602b down-convert the pump illumination 103b of wavelength $\lambda^P_2$ to emit broadband illumination having a central wavelength of $\lambda^E_2$, where $\lambda^E_2 > \lambda^P_2$. The nanocrystals 106b may be selected such that the absorption spectrum of the nanocrystals 106b provide for at least the partial transmission of the broadband illumination containing $\lambda^E_3$. The nanocrystals 106a used to form emission region 602a down-convert the pump illumination 103a of wavelength $\lambda^P_1$ to emit broadband illumination having a central wavelength of $\lambda^E_1$, where $\lambda^E_1 > \Delta^P_1$. The nanocrystals 106a may be selected such that the absorption spectrum of the nanocrystals 106a provide for at least the partial transmission of the broadband illumination containing $\lambda^E_2$. Such an arrangement may result in a collected broadband illumination output 105 that contains illumination generated by each of the emission regions 602a-602e, resulting in an emission spectrum having a spectral content of at least $\lambda^E_1$, $\lambda^E_2$, $\lambda^E_3$, $\lambda^E_4$, and $\lambda^E_5$. In one embodiment, the nanocrystals 106a used to form emission region 602a may be selected such that $\lambda^E_1$ is on the bluer end of the spectrum, while nanocrystals 106e used to form emission region 602e such that $\lambda^E_5$ is on the redder end of the spectrum (relative to $\lambda^E_1$). For example, $\lambda^E_1 < \lambda^E_2 < \lambda^E_3 < \lambda^E_4 < \lambda^E_5$. It is noted herein that such an arrangement is made possible due to the tunability of the emission and absorption spectra of the emission regions 602a-602e (or any other arrangement) through the selection of the nanocrystal materials and the control of the quantum confinement/sizes of the nanocrystals.

It is noted that, while multiple laser sources P1-P5 are depicted in FIGS. 6A and 6B, this arrangement should not be interpreted as a limitation on the scope of the present disclosure and is provided merely for illustrative purposes. For example, the pump illumination 103 used to pump different color emission regions 602a-602e may be provided via a single laser or multiple lasers.

It is further noted that the particular geometry depicted in FIGS. 6A-6B should not be interpreted as a limitation on the scope of the present disclosure and is provided merely for illustrative purposes. It is noted that the scope of the present disclosure should be interpreted to extend to any arrangement of one or more pump sources 102 and emission regions providing for the tunability of emission outputs and absorption spectrums of individual emission regions, through the combination of multiple nanocrystal species (composition and/or size of nanocrystals). Such arrangements may include any arrangement of dots (as in FIGS. 6A-6B), other geometric shapes (e.g., cylinders, rods, pillars), or shells, rings, or layers (e.g., shells or layers of a cylindrical, spherical, or disk structure).

Figure 6C:
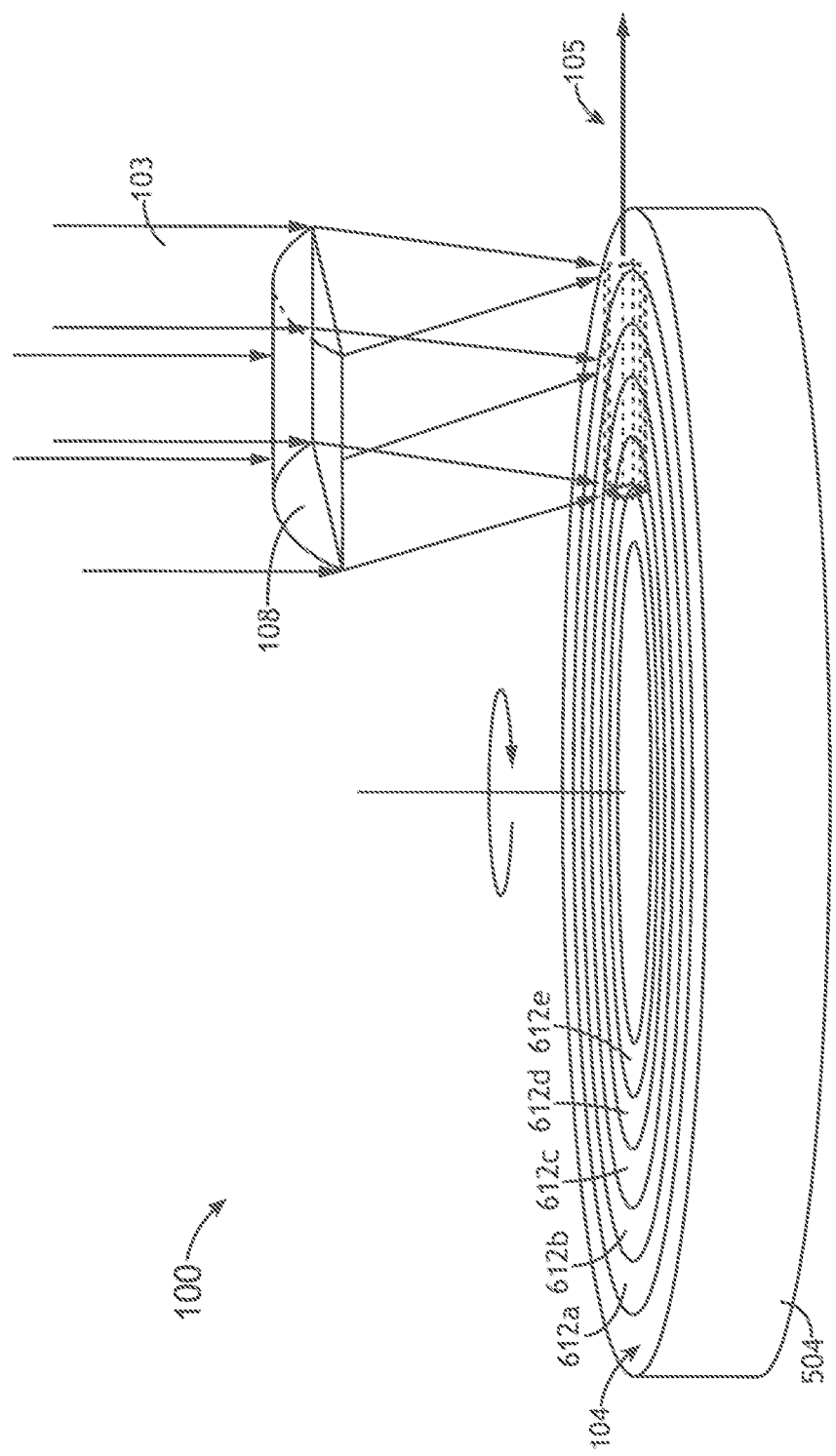
FIG. 6C illustrates a simplified schematic view of a broadband source including a set of concentric discrete emission regions containing nanocrystals disposed on a rotatable substrate, in accordance with one more embodiments of the present disclosure.

FIG. 6C illustrates a simplified schematic view of the broadband source 100 including a set of concentric discrete emission regions containing nanocrystals disposed on a rotatable substrate 504, in accordance with one or more embodiments of the present disclosure. In this embodiment, the set of emission regions 612a-612e are arranged concentrically. For example, each emission region 612a-612e may be formed from nanocrystals that cause the emission regions 612a-612e to emit illumination at different wavelengths, whereby emission region 612e is surrounded by emission region 612d, emission region 612d is surrounded by emission region 612c, emission region 612c is surrounded by emission region 612b, and emission region 612b is surrounded by emission region 612a. The emission regions 612a-612e may be formed in any manner known in the art. For example, each of the emission regions may be formed on the substrate 504 via sol-gel processing such that each region includes different nanocrystal species, which are tuned to create the desired emission and absorption characteristics for the desired concentric regions.

In another embodiment, the pump source 102 and pump illumination optics 108 are arranged to illuminate the emission regions 612a-612e. As in the embodiment depicted in FIGS. 6A-6B, the pump source 102 may include single or multiple lasers. In one embodiment, a single laser beam may be used to illuminate the emission regions. In another embodiment, multiple lasers may be used to illuminate the different emission regions 612a-612e. It is noted that the embodiments related to the tunability of the emission regions 602a-602e discussed previously herein should be interpreted to extend to the configuration depicted in FIG. 6C.

In one embodiment, each of the nanocrystal species used to form the emission regions 612a-612e may be selected such that each successive concentric emission region is at least partially transparent to the broadband illumination emitted by the previous inner emission region. In one embodiment, the size and/or material composition of the emission regions 612a-612e may be selected in such a way that redder-emitting emission regions are located in the center area of the substrate 502 and bluer-emitting emission regions are located toward the outer edge of the substrate 502. In such an arrangement, the redder-wavelength light emitted by nanocrystals at the center of the substrate 502 propagates through the active media of bluer-wavelength emitting nanocrystals.

Figure 6D:
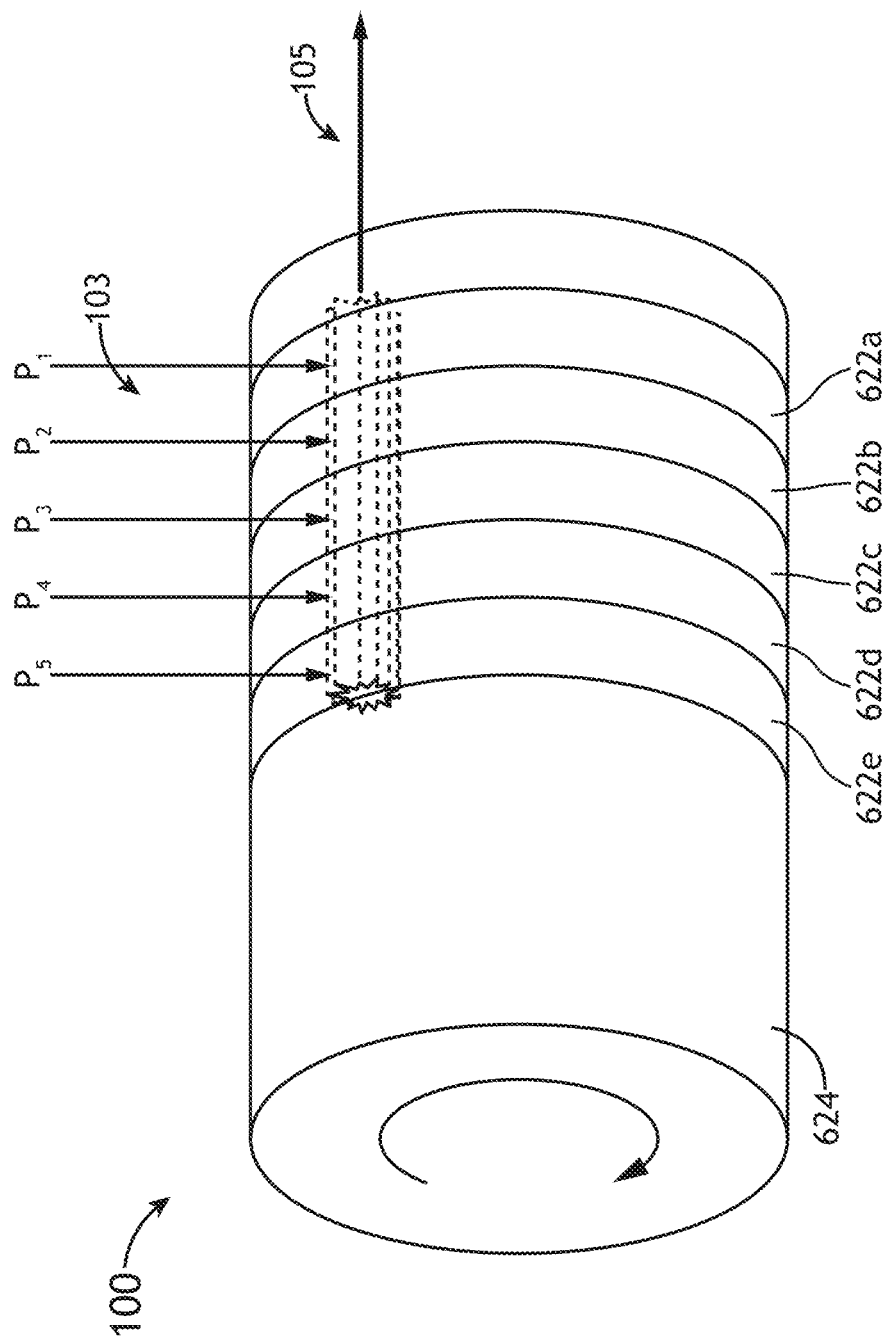
FIG. 6D illustrates a simplified schematic view of a broadband source including a set of discrete emission regions containing nanocrystals disposed on a rotatable cylinder or drum.

Although this embodiment is described in the context of rotatable substrate 504, described previously herein, the scope of the present disclosure is not limited to such a configuration. The embodiment depicted in FIG. 6C may be extended to any substrate configuration that allows for the formation of successive emission regions of different nanocrystals. For example, as illustrated in FIG. 6D, the broadband source 100 may include, but is not limited to, a set of discrete emission regions 622a-622e formed within an active medium containing nanocrystals disposed on a rotatable cylinder or drum 624.

Figure 7:
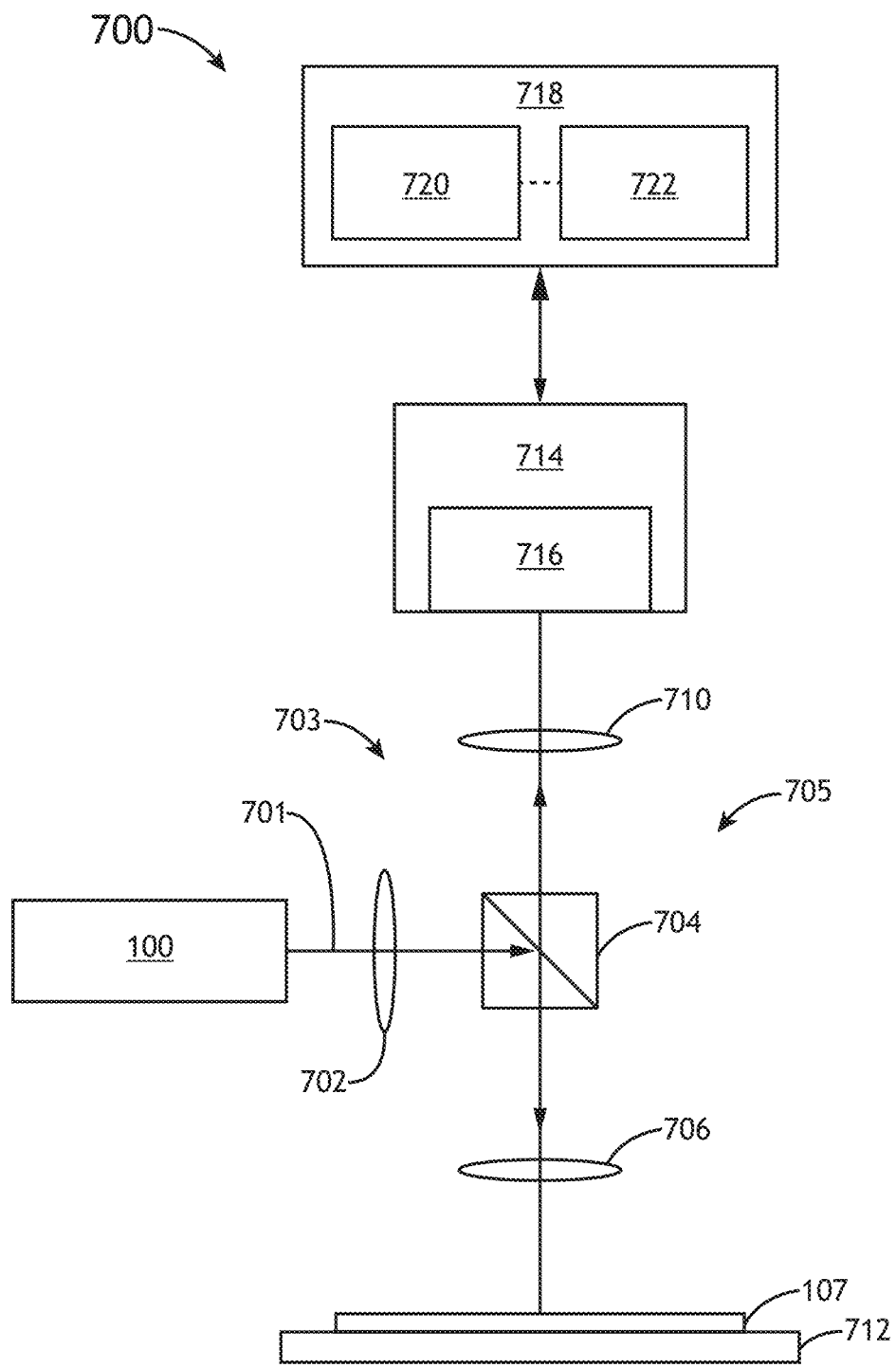
FIG. 7 illustrates a simplified schematic view of an inspection and/or metrology system implementing the broadband illumination source, in accordance with one or more embodiments of the present disclosure.

FIG. 7 illustrates a simplified schematic diagram of an optical characterization system 700, in accordance with one or more embodiments of the present disclosure. The optical characterization system 700 may comprise an inspection system and/or a metrology system. System 700 may be configured to perform inspection, optical metrology and/or any form of imaging on a sample 107. Sample 107 may include any sample known in the art including, but not limited to, a wafer, a reticle, a photomask, and the like. It is noted that system 700 may incorporate one or more of the various embodiments of the broadband source 100 described throughout the present disclosure. In one embodiment, system 700 includes the broadband illumination source 100, an illumination arm 703, a collection arm 705, a detector 714, and a controller 718 including one or more processors 720 and memory 722.

In one embodiment, sample 107 is disposed on a stage assembly 712 to facilitate movement of sample 107. Stage assembly 712 may include any stage assembly 712 known in the art including, but not limited to, an X-Y stage or an R-θ stage. In another embodiment, stage assembly 712 is capable of adjusting the height of sample 107 during inspection or imaging to maintain focus on the sample 107.

In another embodiment, the illumination arm 703 is configured to direct illumination 701 from the broadband source 100 to the sample 107. The illumination arm 703 may include any number and type of optical components known in the art. In one embodiment, the illumination arm 703 includes one or more optical elements 702, a beam splitter 704, and an objective lens 706. In this regard, illumination arm 703 may be configured to focus illumination 701 from the illumination source 100 onto the surface of the sample 107. The one or more optical elements 702 may include any optical element or combination of optical elements known in the art including, but not limited to, one or more mirrors, one or more lenses, one or more polarizers, one or more gratings, one or more filters, one or more beam splitters, and the like.

In another embodiment, system 700 includes a collection arm 705 configured to collect light reflected, scattered, diffracted, and/or emitted from sample 107. In another embodiment, collection arm 705 may direct and/or focus the light from the sample 107 to a sensor 716 of a detector assembly 714. It is noted that sensor 716 and detector assembly 714 may include any sensor and detector assembly known in the art. The sensor 716 may include, but is not limited to, a CCD sensor or a CCD-TDI sensor. Further, sensor 716 may include, but is not limited to, a line sensor or an electron-bombarded line sensor.

In another embodiment, detector assembly 714 is communicatively coupled to a controller 718 including one or more processors 720 and memory 722. For example, the one or more processors 720 may be communicatively coupled to memory 722, wherein the one or more processors 720 are configured to execute a set of program instructions stored on memory 722. In one embodiment, the one or more processors 720 are configured to analyze the output of detector assembly 714. In one embodiment, the set of program instructions are configured to cause the one or more processors 720 to analyze one or more characteristics of sample 107. In another embodiment, the set of program instructions are configured to cause the one or more processors 720 to modify one or more characteristics of system 700 in order to maintain focus on the sample 107 and/or the sensor 716. For example, the one or more processors 720 may be configured to adjust the objective lens 706 or one or more optical elements 702 in order to focus illumination 701 from illumination source 100 onto the surface of the sample 107. By way of another example, the one or more processors 720 may be configured to adjust the objective lens 706 and/or one or more optical elements 710 in order to collect illumination from the surface of the sample 107 and focus the collected illumination on the sensor 716.

It is noted that the system 700 may be configured in any optical configuration known in the art including, but not limited to, a dark-field configuration, a bright-field orientation, and the like.

Additional details of various embodiments of inspection or metrology system 700 are described in U.S. patent application Ser. No. 13/554,954, entitled "Wafer Inspection System," filed on Jul. 9, 2012; U.S. Published Patent Application 2009/0180176, entitled "Split Field Inspection System Using Small Catadioptric Objectives," published on Jul. 16, 2009; U.S. Published Patent Application 2007/0002465, entitled "Beam Delivery System for Laser Dark-Field Illumination in a Catadioptric Optical System," published on Jan. 4, 2007; U.S. Pat. No. 5,999,310, entitled "Ultra-broadband UV Microscope Imaging System with Wide Range Zoom Capability," issued on Dec. 7, 1999; U.S. Pat. No. 7,525,649 entitled "Surface Inspection System Using Laser Line Illumination with Two Dimensional Imaging," issued on Apr. 28, 2009; U.S. Published Patent Application 2013/0114085, entitled "Dynamically Adjustable Semiconductor Metrology System," by Wang et al. and published on May 9, 2013; U.S. Pat. No. 5,608,526, entitled "Focused Beam Spectroscopic Ellipsometry Method and System" by Piwonka-Corle et al., issued on Mar. 4, 1997; and U.S. Pat. No. 6,297,880, entitled "Apparatus for Analysing Multi-Layer Thin Film Stacks on Semiconductors," by Rosencwaig et al., issued on Oct. 2, 2001, which are each incorporated herein by reference in their entirety.

Figure 8:
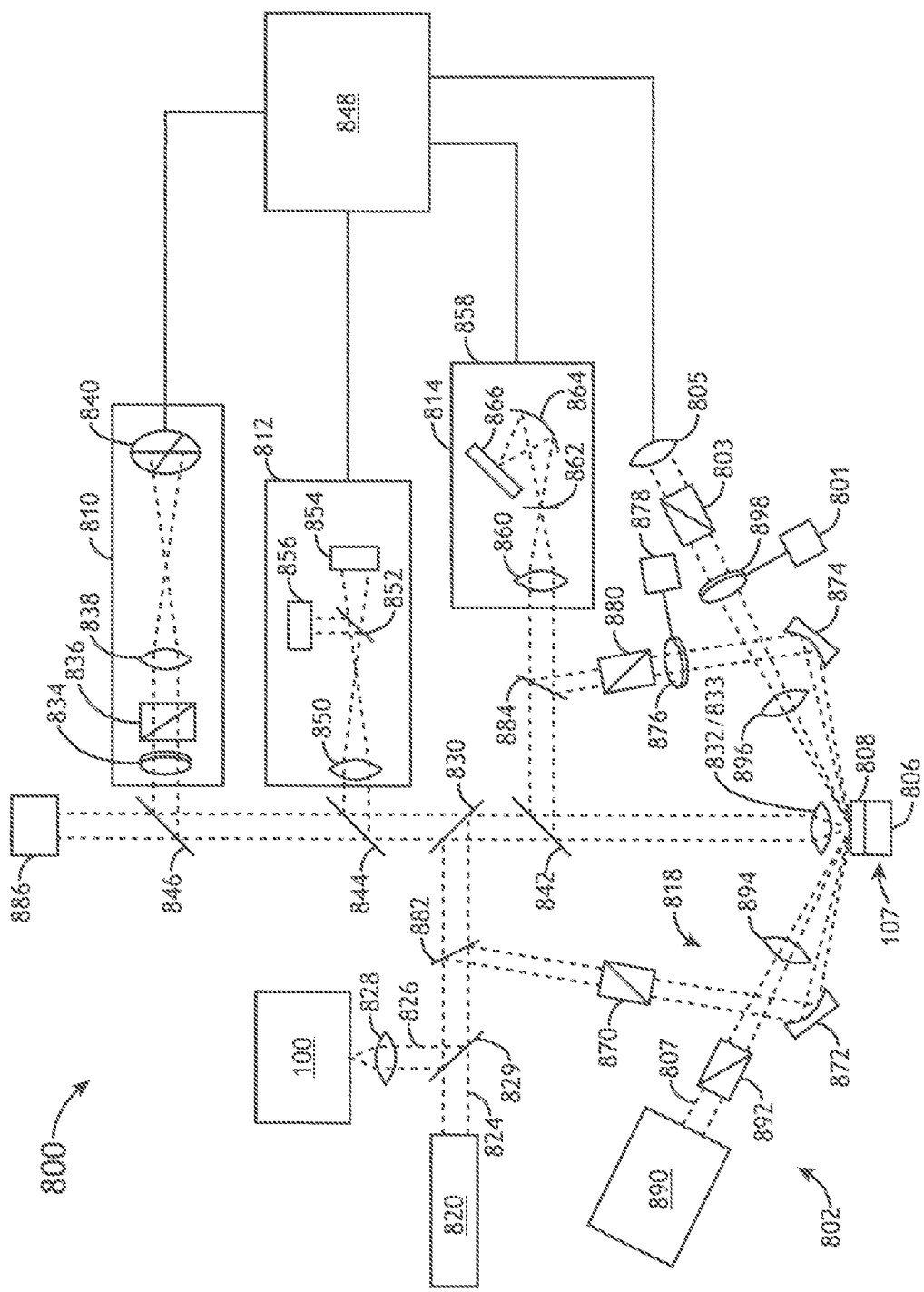
FIG. 8 illustrates a simplified schematic view of an inspection and/or metrology system implementing the broadband illumination source, in accordance with one or more embodiments of the present disclosure.

FIG. 8 illustrates a simplified schematic diagram of an inspection and/or metrology system 800, in accordance with one or more embodiments of the present disclosure. In one embodiment, system 800 may include multiple measurement and/or inspection subsystems which are configured to implement broadband illumination source 100 as a light source.

In one embodiment, system 800 may include a Beam Profile Ellipsometer (BPE) 810, a Beam Profile Reflectometer (BPR) 812, a Broadband Reflective Spectrometer (BRS) 814, a Broadband Spectroscopic Ellipsometer (BSE) 818, and a reference ellipsometer 802. In one embodiment, these optical measurement devices may utilize as few as three optical sources including, but not limited to, lasers 820, 890, and illumination source 100, as described previously herein. The probe beams 824, 826 are reflected by mirror 830, and pass through mirror 842 to a sample 107.

In another embodiment, laser 820 may generate a probe beam 824, and illumination source 100 may generate probe beam 826 (which is collimated by lens 828 and directed along the same path as probe beam 824 by mirror 829). In another embodiment, laser 820 may be a solid state laser diode which emits a linearly polarized 3 mW beam at a visible or near IR wavelength such as a wavelength near 670 nm.

In one embodiment, probe beams 824, 826 are focused onto the surface of the sample 107 via one or more lenses 832, 833. Lenses 832, 833 may be mounted in a turret (not shown) and are alternately movable into the path of probe beams 824, 826. Lenses 832, 833 may include any lens known in the art. For example, lens 832 may be a microscope objective lens with a high numerical aperture (on the order of 0.90 NA) to create a large spread of angles of incidence with respect to the sample surface, and to create a spot size of about one micron in diameter. By way of another example, lens 833 may be a reflective lens having a lower numerical aperture (on the order of 0.1 to 0.4 NA) and capable of focusing broadband light to a spot size of about 5-20 μm. It is noted herein that the use of the term 'lens' in the present disclosure may include curved mirrors and optics that comprise a combination of mirrors and lenses. It is further noted that, because some embodiments of the present disclosure incorporate light sources emitting wavelengths over a spectrum from the UV to the IR, curved mirrors can be conveniently used for focusing the light with minimal chromatic aberration.

Beam profile ellipsometry (BPE) is discussed in U.S. Pat. No. 5,181,080, issued Jan. 19, 1993, which is incorporated herein by reference. In one embodiment, BPE 810 may include a quarter-wave plate 834, polarizer 836, lens 838, and a quad sensor 840. In another embodiment, linearly polarized probe beam 824 may be focused onto sample 107 by lens 832. In another embodiment, light reflected from the surface of sample 107 may pass up through lens 832, mirrors 842, 830, 844, and be directed into BPE 810 by mirror 846. The positions of the rays within the reflected probe beam correspond to specific angles of incidence with respect to the surface of the sample 107. In one embodiment, quarter-wave plate 834 may retard the phase of one of the polarization states of the beam by 90 degrees. In another embodiment, linear polarizer 836 may cause the two polarization states of the beam to interfere with each other. For maximum signal, the axis of the polarizer 836 may be oriented at an angle of 45 degrees with respect to the fast and slow axis of the quarter-wave plate 834. In another embodiment, sensor 840 may be a quad-cell sensor with four radially disposed quadrants. In this regard, each of the four radially disposed quadrants may each intercept one quarter of the probe beam and generate a separate output signal proportional to the power of the portion of the probe beam striking that quadrant. In one embodiment, output signals from each quadrant are sent to one or more processors 848. As discussed in U.S. Pat. No. 5,181,080, by monitoring the change in the polarization state of the beam, ellipsometric information, such as LP and A, can be determined.

In one embodiment, system 800 may include a beam profile reflectometry (BPR) 812. Beam profile reflectometry (BPR) is discussed in U.S. Pat. No. 4,999,014, issued on Mar. 12, 1991, which is incorporated herein by reference. In one embodiment, BPR 812 may include a lens 850, beam splitter 852, and two linear sensor arrays 854 and 856 to measure the reflectance of the sample 107. In one embodiment, linearly polarized probe beam 824 may be focused onto sample 107 by lens 832, with various rays within the beam striking the surface of the sample 107 at a range of angles of incidence. In another embodiment, light reflected from the sample 107 surface may pass up through lens 832, mirrors 842 and 830, and be directed into BPR 812 by mirror 844. The positions of the rays within the reflected probe beam correspond to specific angles of incidence with respect to the surface of the sample 107. In one embodiment, lens 850 spatially spreads the beam two-dimensionally. In another embodiment, beam splitter 852 may separate the s and p components of the beam. In another embodiment, sensor arrays 854 and 856 may be oriented orthogonal to each other to isolate information about s and p polarized light. It is noted that the higher angles of incidence rays will fall closer to the opposed ends of the arrays. It is further noted that the output from each element in the sensor arrays 854, 856 will correspond to different angles of incidence.

In another embodiment, sensor arrays 854, 856 may measure the intensity across the reflected probe beam as a function of the angle of incidence with respect to the sample 107 surface. It is noted herein that sensor arrays 854, 856 may comprise one or more line sensors. In another embodiment, one or more processors 848 may receive the output of the sensor arrays 854, 856, and derive the thickness and refractive index of the thin film layer 808 based on these angular dependent intensity measurements by utilizing various types of modeling algorithms. Optimization routines which use iterative processes such as least square fitting routines are typically employed. One example of this type of optimization routine is described in "Multiparameter Measurements of Thin Films Using Beam-Profile Reflectivity," Fanton et al., Journal of Applied Physics, Vol. 73, No. 11, p.7035, 1993. Another example appears in "Simultaneous Measurement of Six Layers in a Silicon on Insulator Film Stack Using Spectrophotometry and Beam Profile Reflectometry," Leng et al., Journal of Applied Physics, Vol. 81, No. 8, page 3570, 1997. Both of these publications are incorporated herein by reference.

In another embodiment, system 800 may include a broadband reflective spectrometer (BRS) 814. In one embodiment, BRS 814 may simultaneously probe the sample 107 with multiple wavelengths of light. In another embodiment, BRS 814 may use lenses 832, 833 to direct light to the surface of the sample 107. In another embodiment, BRS 814 may include a broadband spectrometer 858. It is noted that broadband spectrometer 858 may include any broadband spectrometer known in the art. In one embodiment, broadband spectrometer 858 may include a lens 860, aperture 862, dispersive element 864, and sensor array 866. In one embodiment, probe beam 826 from illumination source 100 may be focused onto sample 107 by lens 832. Light reflected from the surface of the sample 107 may pass up through lens 832, and be directed by mirror 842 (through mirror 884) to broadband spectrometer 858. In one embodiment, lens 860 may focus the probe beam through aperture 862, which defines a spot in the field of view on the sample 107 surface to analyze.

In one embodiment, dispersive element 864 (e.g., diffraction grating, prism, holographic plate, and the like) angularly disperses the beam as a function of wavelength to individual sensor elements contained in the sensor array 866. The different sensor elements may measure the optical intensities of the different wavelengths of light contained in the probe beam. In a preferred embodiment, sensor array 866 comprises a line sensor. In another embodiment, dispersive element 864 may also be configured to disperse the light as a function of wavelength in one direction, and as a function of the angle of incidence with respect to the sample 107 surface in an orthogonal direction, such that simultaneous measurements as a function of both wavelength and angle of incidence are possible. In such an embodiment, sensor array 866 may comprise a line sensor configured so as to simultaneously collect 2 or 3 spectra, each spectrum corresponding to a different range of angles of incidence. In another embodiment, one or more processors 848 may process the intensity information measured by the sensor array 866. It is noted that, when only a subset of the wavelengths is needed for a specific measurement (e.g., if only visible wavelengths are needed), a refractive lens may be used for the measurements. It is further noted that, when IR and/or UV are needed for a specific measurement, reflective lens 833 may be used instead of focusing lens 832. In one embodiment, a turret (not shown) containing lenses 832, 833 may be rotated such that reflective lens 833 is aligned in probe beam 826. It is noted herein that reflective lens 833 may be necessary because refractive lenses may be unable to focus a wide range of wavelengths onto the sample 107 without substantial chromatic aberration.

In one embodiment, system 800 may include broadband spectroscopic ellipsometry (BSE) 818. Broadband spectroscopic ellipsometry (BSE) is discussed in U.S. Pat. No. 5,877,859, issued on Mar. 2, 1999 to Aspnes et al., which is incorporated by reference herein. In one embodiment, BSE 818 may include a polarizer 870, focusing mirror 872, collimating mirror 874, rotating compensator 876, and analyzer 880. In one embodiment, mirror 882 may direct at least part of probe beam 826 to polarizer 870, which creates a known polarization state for the probe beam 826. In a preferred embodiment, the polarization state for the probe beam 826 is a linear polarization. In another embodiment, mirror 872 focuses the beam onto the sample 107 surface at an oblique angle, ideally on the order of 70 degrees to the normal of the sample 107 surface. Based upon well-known ellipsometric principles, the reflected beam will generally have a mixed linear and circular polarization state after interacting with the sample 107, based upon the composition and thickness of the sample's 107 film 808 and substrate 806. In another embodiment, reflected beam is collimated by mirror 874, which directs the beam to the rotating compensator 876.

In another embodiment, compensator 876 introduces a relative phase delay δ (phase retardation) between a pair of mutually orthogonal polarized optical beam components. In another embodiment, compensator 876 is rotated at an angular velocity ω about an axis substantially parallel to the propagation direction of the beam, preferably by an electric motor 878. In another embodiment, analyzer 880 mixes the polarization states incident on it. In a preferred embodiment, analyzer 880 is another linear polarizer. By measuring the light transmitted by analyzer 880, the polarization state of the reflected probe beam 826 may be determined. In another embodiment, mirror 884 directs the beam to spectrometer 858, which simultaneously measures on sensor 866 the intensities of the different wavelengths of light in the reflected probe beam that pass through the compensator/analyzer combination. In a preferred embodiment, sensor 866 comprises a line sensor. In another embodiment, in order to solve for sample characteristics, such as the ellipsometric values LP and A (as described in U.S. Pat. No. 5,877,859) one or more processors 848 receive the output of the sensor 866, and processes the intensity information measured by the sensor 866 as a function of wavelength and the azimuth (rotational) angle of the compensator 876 about its axis of rotation.

In one embodiment, detector 886 may be positioned above mirror 846, and can be used to view reflected beams off of the sample 107 for alignment and focus purposes. It is noted herein that detector 886 may include any detector assembly known in the art.

In one embodiment, in order to calibrate BPE 810, BPR 812, BRS 814, and BSE 818, system 800 may include the wavelength stable calibration reference ellipsometer 802 that may be used in conjunction with a reference sample 107. In one embodiment, ellipsometer 802 may include a light source 890, polarizer 892, lenses 894, 896, rotating compensator 898, analyzer 803, and detector 805.

In one embodiment, light source 890 produces a quasi-monochromatic probe beam 807 having a known stable wavelength and stable intensity. The wavelength of beam 807, which is a known constant or a measured value, is provided to one or more processors 848 such that ellipsometer 802 can accurately calibrate the optical measurement devices in system 800.

In another embodiment, beam 807 interacts with polarizer 892 to create a known polarization state. In a preferred embodiment, polarizer 892 is a linear polarizer made from a quartz Rochon prism. However, it is noted that, in general, the polarization does not necessarily have to be linear, nor even complete. Polarizer 892 may also be made from calcite or $MgF_2$. In one embodiment, the azimuth angle of polarizer 892 is oriented such that the plane of the electric vector associated with the linearly polarized beam exiting from the polarizer 892 is at a known angle with respect to the plane of incidence (defined by the propagation direction of the beam 807 and the normal to the surface of sample 107). The azimuth angle is preferably selected to be on the order of 30 degrees because the sensitivity is optimized when the reflected intensities of the P and S polarized components are approximately balanced. It is noted herein that polarizer 892 may be omitted if the light source 890 emits light with the desired known polarization state.

In one embodiment, beam 807 is focused onto the sample 107 by lens 894 at an oblique angle. In a preferred embodiment, beam 807 is incident on sample 107 at an angle on the order of 70 degrees to the normal of the sample 107 surface. It is noted herein that sensitivity to sample 107 properties is maximized in the vicinity of the Brewster or pseudo-Brewster angle of a material. Based upon well-known ellipsometric principles, the reflected beam will generally have a mixed linear and circular polarization state after interacting with the sample 107, as compared to the linear polarization state of the incoming beam 807.

In another embodiment, lens 896 collimates beam 807 after its reflection off the sample 107. In another embodiment, beam 807 then passes through the rotating compensator (retarder) 898, which introduces a relative phase delay δr (phase retardation) between a pair of mutually orthogonal polarized optical beam components. The amount of phase retardation is a function of the wavelength, the dispersion characteristics of the material used to form the compensator, and the thickness of the compensator. In one embodiment, compensator 898 is rotated at an angular velocity ωr about an axis substantially parallel to the propagation direction of beam 807, preferably by an electric motor 801. It is noted that compensator 898 may include any conventional wave-plate compensator known in the art. For example, the compensator may include a wave-plate compensator made of crystal quartz. The thickness and material of the compensator 898 may be selected such that a desired phase retardation of the beam is induced. Typically, a phase retardation of about 90° is convenient.

In another embodiment, beam 807 interacts with analyzer 803, which serves to mix the polarization states incident on it. In this embodiment, analyzer 803 is another linear polarizer, preferably oriented at an azimuth angle of 45 degrees relative to the plane of incidence. However, it is noted that any optical device that serves to appropriately mix the incoming polarization states can be used as an analyzer 803. In a preferred embodiment, analyzer 803 is a quartz Rochon or Wollaston prism.

It is noted herein that compensator 898 may be located either between the sample 107 and the analyzer 803 (as shown in FIG. 8). Alternatively, compensator 898 may be located between the sample 107 and the polarizer 892. It is further noted that polarizer 870, lenses 894, 896, compensator 898, and analyzer 803 may all be optimized in their construction for the specific wavelength of light produced by light source 890, which maximizes the accuracy of ellipsometer 802.

In another embodiment, beam 807 may enter detector 805, which measures the intensity of the beam passing through the compensator/analyzer combination. In another embodiment, one or more processors 848 process the intensity information measured by the detector 805 to determine the polarization state of the light after interacting with the analyzer 803, and therefore the ellipsometric parameters of the sample 107. This information processing may include measuring beam intensity as a function of the azimuth (rotational) angle of the compensator about its axis of rotation. This measurement of intensity as a function of compensator rotational angle is effectively a measurement of the intensity of beam 807 as a function of time, since the compensator angular velocity is usually known and constant.

U.S. Pat. No. 6,297,880, which issued on Oct. 2, 2001 to Rosenecwaig et al. and is incorporated by reference herein, describes metrology system 800 in further detail. U.S. Pat. No. 6,429,943, which issued on Aug. 6, 2002 to Opsal et al. and is incorporated by reference herein, describes how metrology system 800 may be used for scatterometry measurements. U.S. Pat. No. 5,608,526, which issued on Mar. 4, 1997 to Piwonka-Corle et al. and is incorporated by reference herein, describes an alternative embodiment of metrology system 800 that incorporates a spectroscopic ellipsometer and a spectrophotometer. Either, or both, of the spectroscopic ellipsometer and spectrophotometer may incorporate the broadband illumination source described herein and may be used in methods of measuring a sample described herein.

The one or more processors 720, 848 of the present disclosure may include any one or more processing elements known in the art. In this sense, the one or more processors 720, 848 may include any microprocessor-type device configured to execute software algorithms and/or instructions. In one embodiment, the one or more processors 720, 848 may consist of a desktop computer, mainframe computer system, workstation, image computer, parallel processor, or other computer system (e.g., networked computer) configured to execute a program configured to operate the systems 100, 700, 800, as described throughout the present disclosure. It should be recognized that the steps described throughout the present disclosure may be carried out by a single computer system or, alternatively, multiple computer systems. In general, the term "processor" may be broadly defined to encompass any device having one or more processing elements, which execute program instructions from a non-transitory memory medium 722. Moreover, different subsystems of the various systems disclosed may include processor or logic elements suitable for carrying out at least a portion of the steps described throughout the present disclosure. Therefore, the above description should not be interpreted as a limitation on the present disclosure but merely an illustration.

The memory medium 722 may include any storage medium known in the art suitable for storing program instructions executable by the associated one or more processors 720. For example, the memory medium 722 may include a non-transitory memory medium. For instance, the memory medium 722 may include, but is not limited to, a read-only memory, a random access memory, a magnetic or optical memory device (e.g., disk), a magnetic tape, a solid state drive, and the like. In another embodiment, the memory 722 is configured to store one or more results and/or outputs of the various steps described herein. It is further noted that memory 722 may be housed in a common controller housing with the one or more processors 720. In an alternative embodiment, the memory 722 may be located remotely with respect to the physical location of the processors 720. For instance, the one or more processors 720 may access a remote memory (e.g., server), accessible through a network (e.g., internet, intranet, and the like). In another embodiment, the memory medium 722 maintains program instructions for causing the one or more processors 720 to carry out the various steps described through the present disclosure.

In another embodiment, the systems 100, 700, 800 may include a user interface (not shown). In one embodiment, the user interface is communicatively coupled to the one or more processors 720, 848. In another embodiment, the user interface device may be utilized to accept selections and/or instructions from a user. In some embodiments, described further herein, a display may be used to display data to a user. In turn, a user may input selection and/or instructions (e.g., selection, sizing, and/or position of filter box) responsive to data displayed to the user via the display device.

The user interface device may include any user interface known in the art. For example, the user interface may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel mounted input device, or the like. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of a display device is suitable for implementation in the present disclosure.

The display device may include any display device known in the art. In one embodiment, the display device may include, but is not limited to, a liquid crystal display (LCD), an organic light-emitting diode (OLED) based display or a CRT display. Those skilled in the art should recognize that a variety of display devices may be suitable for implementation in the present disclosure and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present disclosure.

In some embodiments, the systems 100, 700, 800, as described herein, may be configured as a "stand alone tool" or a tool that is not physically coupled to a process tool. In other embodiments, such an inspection or metrology system may be coupled to a process tool (not shown) by a transmission medium, which may include wired and/or wireless portions. The process tool may include any process tool known in the art such as a lithography tool, an etch tool, a deposition tool, a polishing tool, a plating tool, a cleaning tool, or an ion implantation tool. The results of inspection or measurement performed by the systems described herein may be used to alter a parameter of a process or a process tool using a feedback control technique, a feedforward control technique, and/or an in-situ control technique. The parameter of the process or the process tool may be altered manually or automatically.

The embodiments of the systems 100, 700, 800 may be further configured as described herein. In addition, the systems 100, 700, 800 may be configured to perform any other step(s) of any of the method embodiment(s) described herein.

Figure 9:
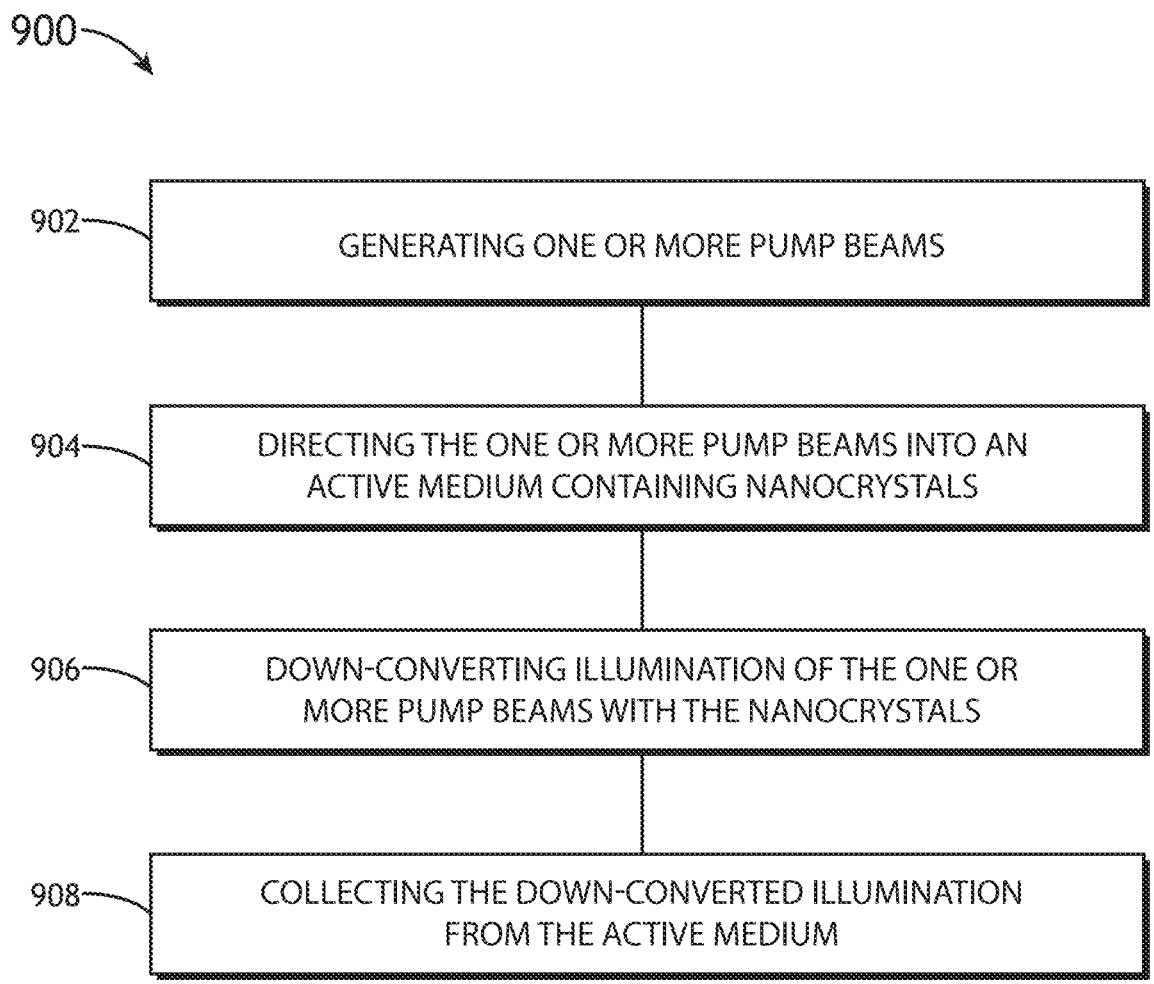
FIG. 9 illustrates a flow diagram depicting a method for generating broadband illumination, in accordance with one or more embodiments of the present disclosure.

FIG. 9 illustrates a flow diagram depicting a method for generating broadband illumination, in accordance with one or more embodiments of the present disclosure. It is noted herein that the steps of method 900 may be implemented all or in part by systems 100, 700, or 800. It is further recognized, however, that the method 900 is not limited to the systems 100, 700, or 800, in that additional or alternative system-level embodiments may carry out all or part of the steps of method 900.

In step 902, one or more pump beams are generated. For example, as shown in FIGS. 1-2, one or more pump lasers may be used to generate one or more pump beams 103.

In step 904, the one or more pump beams are directed into an active medium containing one or more nanocrystals. For example, as shown in FIGS. 1-2, one or more pump illumination optics 108 (e.g., mirror, lens, etc.) are used to direct and/or focus the one or more pump beams into the active medium 104.

In step 906, the nanocrystals contained within (or form) the active medium 104 down-convert the illumination of the one or more pump beams into broadband illumination. For example, as shown in FIGS. 1-2, the active medium down-converts the illumination from the one or more pump beams to generate down-converted illumination that is red-shifted relative to the illumination of the one or more pump beams 103.

In step 908, the down-converted illumination is collected from the active medium 104. For example, as shown in FIG. 2, one or more collection optics 110 serve to collect at least a portion of the down-converted broadband emission 105 from the active medium 104. In turn, the collection optics 110 may further be used to direct the broadband emission 105 to one or more additional optics (e.g., input optics for an inspection tool or metrology tool).

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly interactable and/or wirelessly interacting components and/or logically interacting and/or logically interactable components.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

The invention claimed is:

1. A broadband illumination source comprising:
a pump source configured to generate pump illumination;
an active medium containing a plurality of nanocrystals; and
one or more pump illumination optics,
wherein the one or more pump illumination optics are configured to direct pump illumination into the active medium,
wherein the active medium is configured to emit broadband illumination by down converting a portion of the pump illumination via photoluminescence, wherein the active media has an index of refraction suitable to establish a wave guide mode within a cylindrical volume of the active media for the pump illumination, wherein the pump illumination and the emitted broadband illumination are transmitted along an elongated volume of the active medium.

2. The broadband illumination source of claim 1, further comprising:
one or more collection optics configured to collect a portion of the broadband illumination from the active medium and direct the broadband illumination to one or more additional optical elements.

3. The broadband illumination source of claim 1, wherein the pump source comprises:
one or more lasers.

4. The broadband illumination source of claim 3, wherein the one or more lasers comprise:
one or more lasers configured to generate visible light.

5. The broadband illumination source of claim 4, wherein the one or more lasers comprise:
at least one of a green laser or a blue laser.

6. The broadband illumination source of claim 1, wherein the broadband illumination emitted by the plurality of nanocrystals comprises:
at least one of visible light or near infrared light.

7. The broadband illumination source of claim 1, wherein the plurality of nanocrystals comprises:
a plurality of at least one of CdSe nanocrystals, CdS nanocrystals, PbS nanocrystals, ZnSe nanocrystals, or CdTe nanocrystals.

8. The broadband illumination source of claim 1, wherein the plurality of nanocrystals comprises:
a plurality of core-shell nanocrystals.

9. The broadband illumination source of claim 1, wherein the plurality of nanocrystals comprises:
a mixture of two or more nanocrystal materials.

10. The broadband illumination source of claim 1, wherein the plurality of nanocrystals are formed within the active medium in a plurality of monolayers.

11. The broadband illumination source of claim 1, wherein the plurality of nanocrystals are formed with a surface density between approximately $1 \times 10^{12}$ and $1 \times 10^{14}$ nanocrystals/mm$^2$.

12. The broadband illumination source of claim 1, wherein at least some of the plurality of nanocrystals have an average size between approximately 1 and 10 nm.

13. The broadband illumination source of claim 1, wherein the pump illumination optics comprise:
at least one of a mirror or a lens.

14. The broadband illumination source of claim 1, wherein the active medium comprises:
a volume of liquid material, wherein the active medium is at least one of a solution, a suspension, or a colloid.

15. The broadband illumination source of claim 1, wherein the active medium comprises:
a glass, wherein the plurality of nanocrystals are formed in a matrix of the glass.

16. The broadband illumination source of claim 1, wherein the active medium comprises:
a sol-gel material, wherein the plurality of nanocrystals are formed in a matrix of the sol-gel material.

17. The broadband illumination source of claim 1, wherein the active medium comprises:
a solid material, wherein the plurality of nanocrystals are disposed on or within the solid material.

18. The broadband illumination source of claim 17, wherein the active medium comprises:
a solid substrate, wherein the plurality of nanocrystals are disposed on the solid substrate.

19. The broadband illumination source of claim 17, wherein the active medium comprises:
one or more fibers impregnated with the plurality of nanocrystals.

20. The broadband illumination source of claim 1, wherein the active medium has a cylindrical shape.

21. The broadband illumination source of claim 20, wherein the pump illumination is transversely directed into the active medium.

22. The broadband illumination source of claim 20, wherein the pump illumination is longitudinally directed into the active medium.

23. The broadband illumination source of claim 1, wherein the pump illumination is focused into liquid jet of the active medium.

24. The broadband illumination source of claim 1, wherein the pump illumination is focused into a capillary structure containing the active medium.

25. The broadband illumination source of claim 1, wherein the pump illumination is focused into a dye cell containing the active medium.

26. The broadband illumination source of claim 1, wherein the pump illumination is coupled to the active medium through an end portion of the elongated volume of the active medium.

27. The broadband illumination source of claim 1, wherein the pump illumination is coupled to the active medium through a coupling element disposed along the elongated volume of the active medium.

28. The broadband illumination source of claim 1, further comprising:
one or more thermal management devices.

29. The broadband illumination source of claim 28, wherein the one or more thermal management devices are configured to move at least a portion of the active medium relative to the pump illumination in order to control a local temperature of the active medium.

30. The broadband illumination source of claim 28, wherein the one or more thermal management devices comprises:
a movable substrate, wherein the active medium is formed on the movable substrate.

31. The broadband illumination source of claim 30, wherein the movable substrate comprises:
at least one of a rotatable disk, a rotatable drum, a rotatable ring, or a conveyor.

32. The broadband illumination source of claim 28, wherein the one or more thermal management devices comprises:
one or more fluid transport devices, wherein the active medium is formed within a fluid, wherein the fluid is transported by the one or more fluid transport devices.

33. The broadband illumination source of claim 1, wherein the pump source comprises:
 a plurality of pump lasers, wherein each laser emits pump illumination at a different wavelength.

34. The broadband illumination source of claim 33, wherein pump illumination from each pump laser is focused into a portion of the active medium to create a plurality of emission regions, wherein each emission region emits broadband illumination of a different wavelength range.

35. The broadband illumination source of claim 34, wherein the direction of collection of broadband illumination from the plurality of emission regions is perpendicular to the direction of the pump illumination from the plurality of pump lasers.

36. The broadband illumination source of claim 34, wherein the plurality of emission regions in the active medium are formed with a plurality of nanocrystal species, wherein each emission region corresponds to a particular nanocrystal species.

37. The broadband illumination source of claim 36, wherein the plurality of emission regions are arranged such that a first emission region emits illumination of a first wavelength range and is located on a side of a collecting path nearest collection optics, wherein an at least an additional emission region emits illumination of an additional wavelength range, wherein a central wavelength of the first wavelength range is shorter than a central wavelength of the first wavelength range.

38. The broadband illumination source of claim 37, wherein the first emission region is at least partially transparent to illumination emitted by the at least the additional emission region.

39. The broadband illumination source of claim 37, wherein a size of the nanocrystals of the first emission region is smaller than a size of the nanocrystals of the at least the additional emission region.

40. An optical characterization system comprising:
 a broadband illumination source, wherein the broadband illumination source comprises:
  a pump source configured to generate pump illumination;
  an active medium containing a plurality of nanocrystals; and
  one or more pump illumination optics configured to direct pump illumination into the active medium, wherein the active medium is configured to emit broadband illumination by down converting a portion of the pump illumination via photoluminescence, wherein the active media has an index of refraction suitable to establish a wave guide mode within a cylindrical volume of the active media for the pump illumination, wherein the pump illumination and the emitted broadband illumination are transmitted along an elongated volume of the active medium, wherein the optical characterization system further comprises:
  one or more source collection optics configured to collect a portion of the broadband illumination from the active medium;
  a detector assembly; and
  a set of characterization optics configured to direct the broadband illumination from the broadband illumination source onto a sample, wherein the set of characterization optics is further configured to direct illumination from the sample to the detector assembly.

41. A method comprising:
generating a pump beam;
directing the pump beam into an active medium containing a plurality of nanocrystals;
generating broadband illumination by down-converting a portion of pump illumination with the plurality of nanocrystals via photoluminescence, wherein the active media has an index of refraction suitable to establish a wave guide mode within a cylindrical volume of the active media for the pump illumination, wherein the pump illumination and the generated broadband illumination are transmitted along an elongated volume of the active medium;
collecting down-converted broadband illumination from the active medium; and
performing at least one of inspection or metrology on a sample with the collected down-converted broadband illumination.

42. The optical characterization system of claim 40, wherein the optical characterization system is configured as at least one of an inspection system or a metrology system.

\* \* \* \* \*